(12) United States Patent
Bolton

(10) Patent No.: US 11,774,408 B1
(45) Date of Patent: *Oct. 3, 2023

(54) SYSTEM FOR DETERMINING THE DENSITY OF A SHEET OF MATERIAL USING A MAGNETIC FORCE FEEDBACK ACTUATOR POSITIONER

(71) Applicant: Boise Cascade Company, Boise, ID (US)

(72) Inventor: David Bolton, Lena, LA (US)

(73) Assignee: Boise Cascade Company, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/587,114

(22) Filed: Jan. 28, 2022

(51) Int. Cl.
*G01N 29/22* (2006.01)
*G01N 29/04* (2006.01)
*G01N 29/27* (2006.01)
*G01N 33/46* (2006.01)

(52) U.S. Cl.
CPC ........... *G01N 29/225* (2013.01); *G01N 29/04* (2013.01); *G01N 29/27* (2013.01); *G01N 33/46* (2013.01); *G01N 2291/0238* (2013.01); *G01N 2291/02818* (2013.01); *G01N 2291/102* (2013.01); *G01N 2291/2698* (2013.01)

(58) Field of Classification Search
CPC .... G01N 33/46; G01N 29/04; G01N 29/2493; G01N 29/27; G01N 2291/0231; G01N 2291/0237; G01N 2291/0238; G01N 2291/02818

See application file for complete search history.

(56) References Cited

U.S. PATENT DOCUMENTS

| | | | | |
|---|---|---|---|---|
| 2003/0001595 | A1* | 1/2003 | Steele | G01N 27/02 324/717 |
| 2005/0268720 | A1* | 12/2005 | Quarry | G01N 29/341 73/627 |
| 2021/0070573 | A1* | 3/2021 | Kimata | G01N 29/4436 |

* cited by examiner

*Primary Examiner* — Suman K Nath
(74) *Attorney, Agent, or Firm* — Hawley Troxell Ennis & Hawley LLP; Philip McKay

(57) ABSTRACT

A density detection system uses a magnetic force feedback actuator positioner to maintain a precise selected pressure between transducer wheels and the surface of a sheet of material as the sheet of material moves through a position between transducer wheel and lift wheel. Consequently, the antiquated mechanical/pneumatic springs/airbags of prior art ultrasonic density detection systems are replaced with a highly responsive magnetic force feedback actuator positioner capable of providing a precise and relatively constant force that can react to the introduction of a sheet of material, and/or variations in the surface of a sheet of material, extremely rapidly without the bounce/recovery oscillations associated with prior art ultrasonic density detection systems. Consequently, precise density measurements of an entire sheet of material can be obtained with unprecedented accuracy.

20 Claims, 16 Drawing Sheets

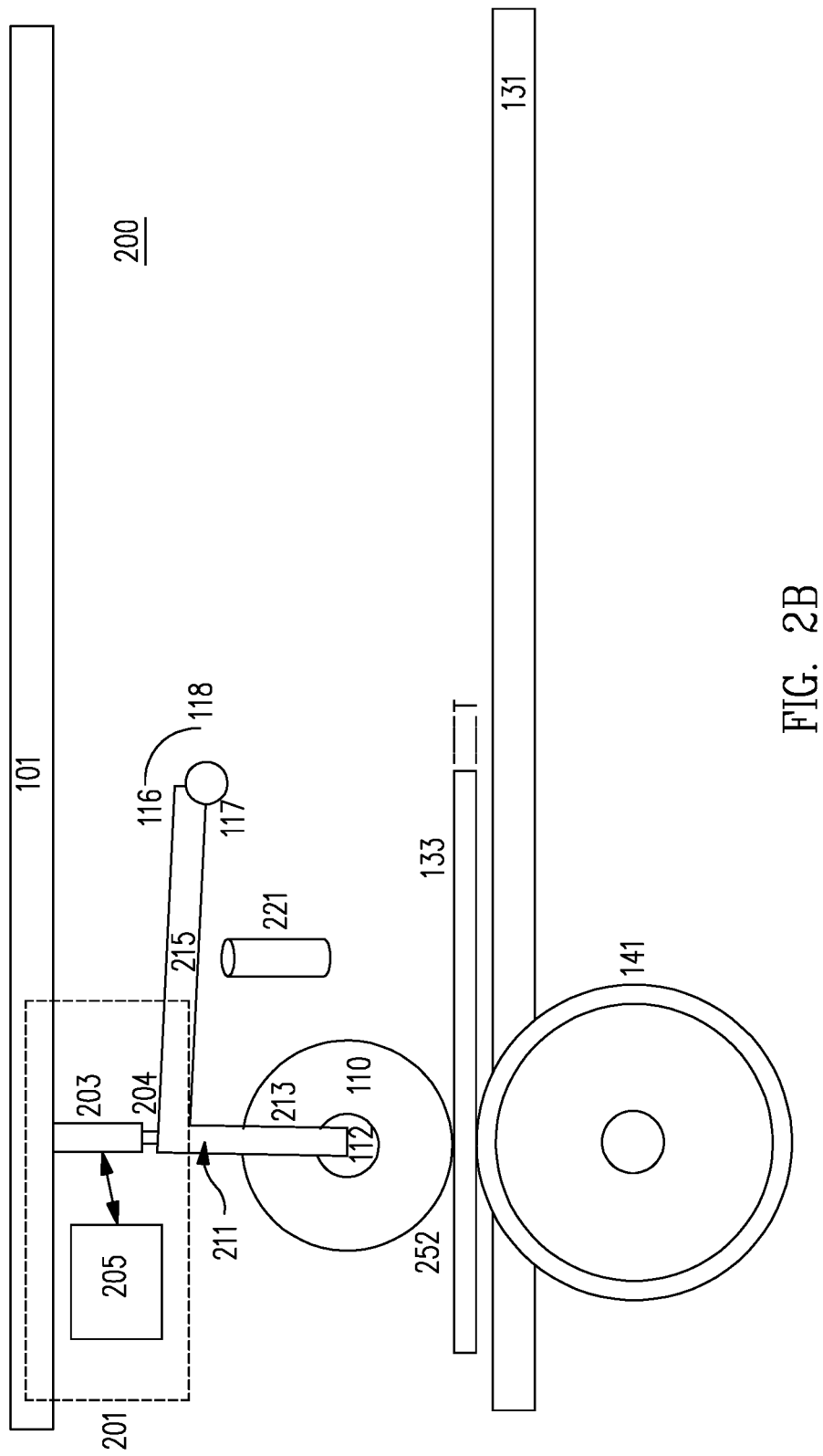

SYSTEM FOR DETERMINING THE DENSITY OF A SHEET OF MATERIAL USING A MAGNETIC FORCE FEEDBACK ACTUATOR POSITIONER

BACKGROUND

There are numerous classes and types of wood products currently used in a virtually limitless variety of construction and other applications. Wood product types include but are not limited to: raw wood products such as logs, debarked blocks, green or dry veneer, and dimensional lumber; intermediate wood components, such as wood I-beam flanges and webs; and layered wood products such as laminated beams, plywood panels, Parallel Laminated Veneer (PLV) products and Laminated Veneer Lumber (LVL) products.

One important physical characteristic for virtually every form of wood product is the density and resulting strength of the wood product. This has become an increasingly important parameter associated with wood products due to new regulations and standards allowing the use of new types of wood products and new uses of existing wood products for various forms of construction. In short, in order to put a given wood product to its best use, and thereby utilize natural resources most effectively, it is becoming more and more important to accurately and consistently determine the density of a wood product and thereby determine the strength of the wood product.

Layered wood products are one example of wood products that are now being used in new ways and for more and more structures. Layered wood products such as plywood, PLV, and LVL are composite products constructed in a factory from both natural wood and one or more chemically blended glues or resins. They are manufactured on a product assembly line and typically fabricated from multiple layers of thin wood, e.g., veneer sheets, assembled with one or more layers of adhesives bonding the veneer sheets together. These layered wood products, sometimes referred to as "man-made" but more commonly referred to as "Engineered Wood," offer several advantages over typical milled lumber. For instance, since layered wood products are fabricated and assembled in a factory under controlled conditions to a set of specific product specifications, they can be stronger, straighter, and more uniform than traditional sawn lumber. In addition, due to their composite nature, layered wood products are much less likely to warp, twist, bow, or shrink than traditional sawn lumber. Layered wood products can also benefit from the multiple grain orientations of the veneer layers and the resulting higher allowable stress capacities than a comparable milled lumber product. However, as discussed herein, to achieve this potential it is often critical that the layers, such as veneer sheets, making up the layered wood products are accurately graded based on determined physical characteristics such as strength/density, surface texture, and moisture content to produce a panel of desired strength, thickness, and visual appearance.

The use of veneer, and particularly veneer that has uniform qualities such as consistent strength/density, allows layered wood products of various dimensions to be created without milling a board of the desired thickness or dimension from a single log or single piece of lumber. This, in turn, allows for much more efficient use of natural resources. Indeed, without the use of various layered wood technologies, such as plywood, PLV, and LVL, the forests of the planet would have been depleted long ago simply to meet the construction needs of the ever-increasing world population. In addition, since layered wood products are fabricated in a factory under controlled specifications, layered wood products can be manufactured to virtually any dimensions desired, including dimensions such as length, width, and height well beyond dimensions that can be provided by milling from even the largest trees.

The use of veneer layers in some layered wood products, such as plywood, PLV, and LVL, can also allow for better structural integrity since any imperfections in a given layer, such as a knot hole, can be mitigated by rotating and/or exchanging layers of veneer so that the imperfection is only one layer deep and is supported by layers of veneer below and above the imperfection in the layered wood products structure. However, these advantages are again dependent on the veneer layers being inspected for consistent features such as density and strength.

In addition to veneer, as mentioned above, the accurate measurement of density and strength of numerous wood products is also highly desirable. In addition, it is often important to accurately measure the density of many non-wood products and materials as well. For instance, other materials include, but are not limited to, plastic extrusion panels, rubber belting, composite panels of any composition, uhmw plastics, plastic and wood laminated materials, and the like.

However, the currently used methods and systems for determining the density, and therefore the strength, of wood products, including veneer sheets, and various other materials is antiquated and extremely inefficient and ineffective in terms of the accuracy of density measurements. This inaccuracy of prior art methods and systems for determining the density of material is due in large part to the rather antiquated mechanical components used with prior art methods and systems for determining the density of material.

For example, one established method and system for determining the density, and therefore strength, of a sheet of material, such as a sheet of veneer or other wood product, involves the use of prior art ultrasonic density detection systems commonly referred to as stress wave analyzers. In their simplest form, prior art ultrasonic density detection systems convey a sheet of material, such as veneer, on a conveyor belt to a density analysis station. At the density analysis station, the sheet of material is run between a rubber lined lift wheel and a transmitter or receiver transducer wheel including a transmitting or receiving transducer element. In this way a portion of the sheet of material is maintained or "pinched" between the lift wheel and the transmitter or receiver transducer wheel.

Herein the term transducer includes either a transmitter, receiver, or both. Consequently, the terms transducer and transmitting transducer can be used interchangeably as can the terms transducer and receiving transducer. Therefore, as a specific example, a transmitting transducer wheel can also be referred to generically as a transducer wheel and a receiving transducer wheel can also be generically as a transducer wheel.

Typically, a minimum of two transducer wheels, and two lift wheels, are utilized in pairs of transmitting transducer wheel/lift wheel and pairs of receiving transducer wheel/lift wheel. In some embodiments two or more transducer wheels and/or lift wheels are used. The sheet of material is then conveyed by the conveyor belt between the transmitting transducer wheel and lift wheel and the receiving transducer wheel and lift wheel so that a first portion of the sheet of material is in contact with the transmitting transducer wheel and lift wheel at the same time a second portion of the sheet of material is in contact with the receiving transducer wheel and lift wheel. The transmitting transducer wheel and lift wheel pair and the receiving transducer wheel and lift wheel are typically separated by a precisely defined distance, often around six feet.

Once the first portion of the sheet of material is between the transmitting transducer wheel and lift wheel and, at the same time, the second portion of the sheet of material is between with the receiving transducer wheel and lift wheel, the transmitting transducer wheel emits an ultrasonic signal (typically in pulses). By separating the transmitting transducer wheel and receiver transducer wheel the defined fixed distance apart, an ultrasonic pulse transmitted into the first portion of the sheet of material by the transmitting transducer wheel then travels through the sheet of material and can be received by the receiving transducer wheel at the second portion of the sheet of material by passing through the sheet of material between the transmitting transducer wheel and receiver transducer wheel.

Since the distance between the transmitting transducer wheel and receiver transducer wheel is known, the density of the sheet of material can be determined by measuring the time it takes the ultrasonic pulse to travel from the transmitting transducer wheel, through the known distance in the sheet of material, to the receiver transducer wheel. The density of the sheet of material can then be determined based on the pulse travel time with shorter travel times indicating higher densities and longer travel times indicating lower densities. The correlation of pulse travel time to density will vary from material to material.

Once the density of the sheet of material is known, this can be used to determine a relative strength of the sheet of material with higher densities generally equating to higher strength and lower densities generally equating to lower strength. The correlation of the density of the sheet of material to the strength of the sheet of material will also vary from material to material.

As the sheet of material moves through the prior art ultrasonic density detection systems and the transmitting transducer wheel/lift wheel and receiver transducer wheel/lift wheel pairs, multiple density readings are captured at multiple locations along the sheet of material, such as veneer. A reading taken every one to two inches along the sheet of material is common.

FIG. 1A is a photograph of a perspective view of a specific illustrative example of a prior art ultrasonic density detection system 100 showing several key components of these prior art systems. Seen in FIG. 1A are prior art support frame 101; prior art pneumatic supply system 107; prior art control panel 106; prior art pneumatic position systems 108; transducer wheels 110; lift wheels 141; and gaps 151 between transducer wheels 110 and lift wheels 141 in the "home" position.

FIG. 1B is a simplified block diagram of a side view of the prior art ultrasonic density detection system 100 of FIG. 1A as viewed in the direction of arrow 120A or 120B. FIG. 1B shows several key components before a sheet of material, such as veneer, is fed into prior art ultrasonic density detection system 100. FIG. 1C is a simplified block diagram of a side view of the prior art ultrasonic density detection system 100 of FIGS. 1A and 1B showing several key components of these prior art systems as a sheet of material, such as veneer, passes through prior art ultrasonic density detection system 100. FIG. 1D is a simplified block diagram of a side view of the prior art ultrasonic density detection system 100 of FIGS. 1A, 1B, and 1C showing several key components of these prior art systems as a sheet of material, such as veneer, exits the prior art ultrasonic density detection system 100.

As seen in FIGS. 1A through 1D, prior art ultrasonic density detection system 100 includes: prior art support frame 101; prior art pneumatic position system air bag 103; prior art counter balance spring 105; transducer wheel 110; prior art traditional transducer lever arm 111 including transducer support 113, transducer lever arm horizontal component 115, transducer lever arm pivot point 117, and prior art transducer lever arm vertical thickness measurement component 119. Also shown in FIGS. 1A through 1D are transducer lever arm stop 121; prior art transducer lever arm thickness/displacement sensor 123; conveyor system 131; sheet of material 133; prior art sheet of material detector 135; lift wheel 141; and gap 151 between transducer wheel 110 and lift wheel 141 in the "home" position.

Of note again is the fact that FIGS. 1A through 1D depict either prior art ultrasonic density detection system 100 viewed in the direction of arrow 120A or as would be viewed in the direction of arrow 120B.

FIG. 1E is a line drawing of a prior art ultrasonic density detection system 100 showing several key components in more detail.

Referring to FIGS. 1A through 1E, prior art support frame 101 is typically made up of several beam and frame components. Typically, these components are made of stainless steel or a similarly solid, and heavy, material to provide support and a framework for prior art ultrasonic density detection system 100.

As seen in FIGS. 1A through 1E, prior art pneumatic position system air bag 103 is coupled to prior art support frame 101 and transducer lever arm horizontal component 115 of prior art traditional transducer lever arm 111. As also seen in FIGS. 1A through 1D, prior art counter balance spring 105 is also coupled to prior art support frame 101 and transducer lever arm horizontal component 115 of prior art traditional transducer lever arm 111.

FIG. 1F is a line drawing showing counter balance spring 105 of prior art ultrasonic density detection system 100 in more detail.

FIG. 1G is a line drawing showing prior art pneumatic position system air bag 103 of prior art ultrasonic density detection system 100 in more detail.

In theory, the purpose of prior art pneumatic position system air bag 103 is to, in combination with prior art counter balance spring 105, provide a theoretically constant pressure on transducer lever arm horizontal component 115 of prior art traditional transducer lever arm 111 which, in turn, theoretically provides a constant pressure on transducer support 113 of prior art traditional transducer lever arm 111 and transducer wheel 110. However, as discussed in more detail below, there are numerous, and significant, limitations on the ability of prior art pneumatic position system air bag 103 in combination with prior art counter balance spring 105 to provide the theoretically constant pressure/force on transducer lever arm horizontal component and transducer wheel 110.

As also seen in FIGS. 1A through 1E, prior art traditional transducer lever arm 111 is movably, i.e., rotationally, operatively coupled to pivot point 117 such that prior art traditional transducer lever arm 111 can rotate/pivot in either direction 116 or 118 about pivot point 117. As seen in FIGS. 1A through 1D, transducer wheel 110 is supported by transducer support 113 of prior art traditional transducer lever arm 111 at rotating center hub 112.

Also seen in FIGS. 1A through 1E is transducer lever arm stop 121. Transducer lever arm stop 121 prevents prior art traditional transducer lever arm 111 from pivoting too far in direction 116 such that transducer wheel 110 comes in contact with lift wheel 141 when there is no sheet of material 133 positioned between transducer wheel 110 and lift wheel 141 (as shown in FIGS. 1B and 1D). Consequently, transducer lever arm stop 121 ensures a minimal gap 151 between transducer wheel 110 and lift wheel 141. Transducer lever arm stop 121 is typically made of urethane or a similar material.

FIG. 1H is a line drawing of a transmitting transducer wheel/lift wheel receiver transducer wheel/lift wheel pair 110/141 of prior art ultrasonic density detection system 100 shown in more detail before a sheet of material, such as veneer, is fed into prior art ultrasonic density detection system 100, as is also depicted in FIGS. 1B and 1D.

FIG. 1I is a line drawing of a transmitting transducer wheel/lift wheel receiver transducer wheel/lift wheel pair 110/141 of prior art ultrasonic density detection system 100 shown in more detail as a sheet of material, such as veneer, passes through prior art ultrasonic density detection system 100, as is also depicted in FIG. 1C.

Also shown in FIGS. 1A through 1E is prior art transducer lever arm thickness/displacement sensor 123 and prior art transducer lever arm vertical thickness measurement component 119. Prior art transducer lever arm thickness/displacement sensor 123 is typically a laser-based device that measures the movement of prior art transducer lever arm vertical thickness measurement component 119 when a sheet of material, such as sheet of material 133, moves between transducer wheel 110 and lift wheel 141 (such as is shown in FIGS. 1C and 1I). The movement of prior art transducer lever arm vertical thickness measurement component 119 when a sheet of material, such as sheet of material 133, moves between transducer wheel 110 and lift wheel 141 measured by prior art transducer lever arm thickness/displacement sensor 123 is then used to determine the thickness of the sheet of material, such as sheet of material 133.

Also shown in FIGS. 1A through 1E is prior art sheet of material detector 135. Typically, prior art sheet of material detector 135 is vision system that detects the presence of a sheet of material, such as sheet of material 133, as the sheet of material moves towards the measurement point between transducer wheel 110 and lift wheel 141.

Finally, FIGS. 1A through 1E include sheet of material 133 to be conveyed to prior art ultrasonic density detection system 100 by conveyor system 131. In various cases, sheet of material 133 is a sheet of veneer, a sheet of any wood product, or a sheet of any material that is to be analyzed by prior art ultrasonic density detection system 100. In various cases, conveyor system 131 is any standard conveyor system such as a traditional conveyor belt.

Referring to FIGS. 1A through 1I, in operation, sheet of material 133 moves along conveyor system 131 to prior art ultrasonic density detection system 100. As seen in FIG. 1B, transducer lever arm stop 121 prevents prior art traditional transducer lever arm 111 from pivoting too far in direction 116 such that transducer wheel 110 comes in contact with lift wheel 141 when there is no sheet of material 133 positioned between transducer wheel 110 and lift wheel 141 (as shown in FIGS. 1B, 1D and 1H).

Consequently, transducer lever arm stop 121 ensures a minimal, or equilibrium, "home" gap 151 between transducer wheel 110 and lift wheel 141. In addition, prior art traditional transducer lever arm 111 and transducer wheel 110 are in the neutral position and prior art transducer lever arm thickness/displacement sensor 123 records this position as the zero, or baseline, position.

As sheet of material 133 moves past prior art sheet of material detector 135, prior art ultrasonic density detection system 100 is triggered to receive and to transmit ultra-sonic pulses to analyze sheet of material 133.

Referring now to FIGS. 1C and 1I, as sheet of material 133 moves through the position between transducer wheel 110 and lift wheel 141, transducer wheel 110 is lifted up so that the gap 152 between transducer wheel 110 and lift wheel 141 of FIG. 1C is greater that gap 151 of FIG. 1B, typically by a distance equal to the thickness of sheet of material 133. This, in turn, causes prior art traditional transducer lever arm 111 to pivot in direction 118 around pivot point 117 as transducer wheel 110 is lifted up. In addition, prior art transducer lever arm thickness/displacement sensor 123 measures the motion of prior art transducer lever arm vertical thickness measurement component 119 when prior art traditional transducer lever arm 111 pivots and this measurement is then used to determine the thickness of sheet of material 133.

As discussed above, and as shown in FIG. 1A, prior art ultrasonic density detection system 100 typically includes a minimum of two transducer wheels and two lift wheels in pairs of transmitting transducer wheels 110/lift wheels 141 and receiving transducer wheels 110/lift wheels 141. As the sheet of material 133 is conveyed by the conveyor system 131 between the transducer wheels 110 and lift wheels 141 a first portion of the sheet of material 133 is in contact with the transducer wheel 110 and lift wheel 141 at the same time a second portion of the sheet of material is in contact with the receiving transducer wheel 110 and lift wheel 141. As noted above, the transducer wheel 110 and lift wheel 141 pair and the receiving transducer wheel 110 and lift wheel 141 are typically separated by a precisely defined distance, often around six feet. However, the accurate measurement of the distance is more important than the distance chosen.

Once the first portion of the sheet of material 133 is between the transmitting transducer wheel 110 and lift wheel 141 and, at the same time, the second portion of the sheet of material 133 is between with the receiving transducer wheel 110 and lift wheel 141, the transmitting transducer wheel emits an ultrasonic signal (typically in pulses). By separating the transducer wheel 110 and receiver transducer wheel 110 by the precisely defined fixed distance, an ultrasonic pulse transmitted into the first portion of the sheet of material 133 by the transmitting transducer wheel 110 then travels through the sheet of material and can be received by the receiving transducer wheel 110 at the second portion of the sheet of material 133 by passing through the sheet of material 133 between the transmitting transducer wheel 110 and receiver transducer wheel 110.

Since the distance between the transmitting transducer wheel 110 and receiver transducer wheel 110 is known, the density of the sheet of material 133 can be determined by measuring the time it takes the ultrasonic pulse to travel from the transmitting transducer wheel 110, through the known distance in the sheet of material 133, to the receiver transducer wheel 110. The density of the sheet of material 133 can then be determined based on the pulse travel time with shorter travel times generally indicating higher densities and longer travel times generally indicating lower densities. The correlation of pulse travel time to density will vary from material to material making up the sheet of material 133.

As the sheet of material 133 moves through prior art ultrasonic density detection system 100 and the position between the transmitting transducer wheel 110/lift wheel 141 and the receiving transducer wheel 110/lift wheel 141 pairs, multiple density readings are captured at multiple locations along the sheet of material 133. Some prior art systems use belt speeds of up to three hundred and fifty feet per minute and a density reading is taken every six inches along the sheet of material 133. However, this distance is typically determined by the speed at which the sheet of material 133 is conveyed by conveyor system 131 or the time interval between transmitted pulse, or both, and therefore can be any distance desired. In some cases speeds of seven hundred and fifty feet per minute can be accommodated using three or more transducer wheels and some systems take a reading every inch.

Once the density of the sheet of material 133 is known, this can be used to determine a relative strength of the sheet of material 133, with higher densities generally equating to higher strength and lower densities generally equating to lower strength.

Referring to FIG. 1D, once the sheet of material 133 passes through the position between the transmitting transducer wheel 110 and lift wheel 141 and the receiving transducer wheel 110 and lift wheel 141, prior art ultrasonic density detection system 100 returns to the starting/neutral positions of FIG. 1B. Consequently, as seen in FIG. 1D, transducer lever arm stop 121 again prevents prior art traditional transducer lever arm 111 from pivoting too far in direction 116 such that the transducer wheel 110 comes in contact with lift wheel 141 when there is no sheet of material 133 positioned between transducer wheel 110 and lift wheel 141.

Consequently, as seen in FIG. 1D, transducer lever arm stop 121 ensures a return to the minimal/home gap 151 between transducer wheel 110 and lift wheel 141. In addition, prior art traditional transducer lever arm 111 and transducer wheel 110 are in the neutral position and prior art transducer lever arm thickness/displacement sensor 123 again records this position as the zero, or baseline, position.

Most of the basic design and components of prior art ultrasonic density detection system 100 discussed above have not significantly changed in over forty years. Consequently, while prior art ultrasonic density detection system 100 can be used to gain a general indication of the strength of a sheet of material, such as veneer, the accuracy and consistency of the measurements obtained from prior art ultrasonic density detection system 100 are far from ideal. As discussed above, it is now often critical that a very accurate measure of the density/strength of a sheet of material, such as veneer, be made. Unfortunately, prior art ultrasonic density detection systems, such as prior art ultrasonic density detection system 100, often fail to rise to the standards of accuracy and consistency required for newer materials and structures.

It is important to note that the accuracy and reliability of density measurements taken using prior art ultrasonic density detection system 100 is almost entirely dependent on keeping a constant pressure on transducer wheel 110, and therefore keeping the pressure/force of transducer wheel 110 on the surface of a sheet of material constant. Any variation in this pressure/force will result in less accurate density readings, with larger variations resulting in larger inaccuracies. Using prior art ultrasonic density detection system 100 this is problematic for several reasons.

First, as noted above, the purpose of prior art pneumatic position system air bag 103 and counter balance spring 105 is to provide a theoretically constant pressure/force on transducer lever arm horizontal component 115 of prior art traditional transducer lever arm 111 which, in turn, theoretically provides a constant pressure/force on transducer support 113 of prior art traditional transducer lever arm 111 and a constant pressure/force transducer wheel 110 and the surface of the sheet of material 133. However, as a relatively antiquated mechanical/pneumatic system, the accuracy and consistency of the pressure/force provided on transducer wheel 110 the surface of the sheet of material 133 by prior art ultrasonic density detection system 100 is not only of questionable accuracy but is also highly inconsistent and subject to significant and unacceptable error and interference.

When a typical prior art ultrasonic density detection system, such as prior art ultrasonic density detection system 100, is used to analyze sheets of veneer, prior art pneumatic position system air bag 103 is kept at a pressure of twenty-five to thirty PSI as read by a standard pressure gauge. Between inaccuracies in gauge reading and the physical make up of prior art pneumatic position system air bag 103, there is often a three PSI or more error in the actual PSI and gauge PSI at any given time. Consequently, as an illustrative example, anytime the gauge reads a desired twenty-six PSI, the actual PSI can be anywhere between twenty two PSI and twenty nine PSI. This, in turn can result in a variance of twelve to sixteen percent in the actual pressure applied by transducer wheel 110 or receiving transducer wheel 110 on the surface of sheet of material. Of course, this can result in a significant variance in density readings from actual density from pulse to pulse in the same sheet of material and can result in a ten percent or more inaccuracy of the measured density of the sheet of material, in this case veneer. For this reason alone, prior art ultrasonic density detection system 100 is unable to provide the accuracy and consistency now required.

Another problem arises when the sheet of material 133 first enters the position between transmitting transducer wheel 110 and lift wheel 141 and receiver transducer wheel 110/lift wheel 141. When the transducer wheels 110 are lifted by the introduction of the sheet of material 133 this "shock" can cause prior art traditional transducer lever arm 111 to over pivot, bounce back and forth, and cause transducer wheels 110 to bounce up and down, i.e., for gap 152 to be highly variable for a period of time as an equilibrium position is reached. During this bounce/recovery time, no reliable density reading can be obtained. In many instances, such as when the sheet of material is veneer, the sheet of material can be moving at a relative high rate of speed, as noted up to seven hundred and fifty feet per minute. Consequently, during this bounce/recovery time, as much as ten percent of the length of the sheet of material 133 passes by while no accurate density reading can be obtained.

The problem arises because prior art ultrasonic density detection system 100 is heavy, i.e., lots of mass and inertia, and being an older mechanical/pneumatic system with no feedback provision, prior art ultrasonic density detection system 100 cannot react quickly or accurately to eliminate, or at least mitigate this issue. Consequently, the bounce/recovery time, and accuracy limitations are currently simply assumed, and accepted as unavoidable, when using prior art ultrasonic density detection system 100. However, as noted, this level of inaccuracy is no longer acceptable in many industries.

FIG. 1J shows a representation 170 of this bounce/recovery time problem. As seen in FIG. 1J, and FIGS. 1B and 1C, at time zero, the sheet of material 133 enters the space between transducer wheel 110 and lift wheel 141 and the transducer lever arm horizontal component 115 of prior art traditional transducer lever arm 111 and transducer wheel 110 are rapidly lifted from the transducer lever arm stop 121. This causes a large displacement and bounce amplitude at 171 and 172. Then at 173 and 174 through 175, 176, 177, 178, and 179, the displacement and bounce amplitude is eventually reduced. However, only at point 181, i.e., time 30, does the displacement and bounce amplitude decrease to the point that a relatively accurate density reading can be taken. As noted, by the time the amplitude oscillations decrease to the point 181 level, ten percent or more of the sheet of material 133 has passed through the space between transducer wheel 110 and lift wheel 141 and virtually useless data is obtained about this portion of sheet of material 133. Clearly this is an unacceptable level of accuracy and consistency for today's demands.

Of note, as the sheet of material 133 moves through the position between transducer wheel 110 and lift wheel 141 past time 30, any irregularities in the surface of sheet of material 133 can also cause transducer wheel 110 to bounce resulting in amplitude oscillations 181, 182, 183, 184 as well. This is also due to fact prior art ultrasonic density detection system 100 is heavy, i.e., lots of mass and inertia and, being an older mechanical/pneumatic system with no feedback provision, prior art ultrasonic density detection system 100 cannot react quickly or accurately. While, these surface irregularity oscillations are not as problematic as the initial bounce oscillations, they can still limit the accuracy of prior art ultrasonic density detection system 100.

Another issue using prior art ultrasonic density detection system 100 is that for various types of material making up sheet of material 133 the goal constant pressure on transducer lever arm horizontal component 115 of prior art traditional transducer lever arm 111 which, in turn, theoretically provides a constant pressure/force on transducer support 113 of prior art traditional transducer lever arm 111 and transducer wheel 110, must be adjusted for the new material. Using prior art ultrasonic density detection system 100 this adjustment is limited to changing the pressure in prior art pneumatic position system air bag 103. However, as discussed above, obtaining accurate pressure in prior art pneumatic position system air bag 103 is difficult and there are no feedback controls for prior art pneumatic position system air bag 103. Consequently, this is highly problematic due to simple physics of compressibility of the prior art pneumatic position system air bag 103 and for varying thicknesses of materials being analyzed.

In addition, the physical shape of lift wheel 141 is subject eccentricity due to manufacturing imperfections and wear and tear resulting from the rebound force associated with the significant mass of prior art ultrasonic density detection system 100. These factors also cause a variation in applied force/pressure on transducer wheel 110 that cannot be effectively identified, measured, or compensated for using prior art ultrasonic density detection system 100.

In addition, as discussed above, prior art ultrasonic density detection system 100 uses prior art transducer lever arm thickness/displacement sensor 123 to determine the thickness of the sheet of material, such as sheet of material 133, by detecting/measuring the movement of prior art transducer lever arm vertical thickness measurement component 119 when a sheet of material, such as sheet of material 133, moves between transducer wheel 110 and lift wheel 141. This system is complicated, requires additional components and maintenance, adds mass in the form of prior art transducer lever arm vertical thickness measurement component 119, and is subject to failure of prior art transducer lever arm thickness/displacement sensor 123.

In addition, as discussed above, prior art ultrasonic density detection system 100 uses prior art sheet of material detector 135. This involves yet more components that must be maintained and are subject to failure. In addition, prior art sheet of material detector 135 is subject to false indicators because prior art sheet of material detector 135 is a purely visual detector and therefore often mistakes debris on conveyor system 131 for a sheet of material, such as sheet of material 133. This also complicates the operation of prior art ultrasonic density detection system 100 and results in inefficient operation of prior art ultrasonic density detection system 100.

As discussed above, prior art ultrasonic density detection systems are largely incapable of providing the consistent and accurate density readings now required in many industries. In addition, prior art ultrasonic density detection systems have many parts and components that are subject to failure, add unnecessary weight to the systems, require significant maintenance, and are subject to failure. Consequently, prior art ultrasonic density detection systems are antiquated, largely ineffective, and are inefficient and expensive to operate.

What is needed is a technical solution to the technical problem of providing a method and system for determining the density of a sheet of material that accurately and consistently determines the density of sheets of material in an effective and efficient manner and is capable of providing the density measurement accuracy now required in many industries.

SUMMARY

Embodiments of the present disclosure provide a technical solution to the long-standing technical problem of providing a method and system for determining the density of a sheet of material that accurately and consistently determines the density of sheets of material in an effective and efficient manner and is capable of providing the density measurement accuracy now needed in many industries.

To this end, the disclosed embodiments utilize a magnetic force feedback actuator positioner to accurately maintain a constant selected pressure/force between transducer elements and the surface of a sheet of material as the sheet of material moves through the position between transmitting transducer element and lift wheel, and/or receiver transducer element and lift wheel. Consequently, according to the disclosed embodiments, the antiquated mechanical/pneumatic springs/airbags of prior art ultrasonic density detection systems are replaced with a highly responsive magnetic force feedback actuator positioner.

The disclosed use of a magnetic force feedback actuator positioner provides not only for a method and system to maintain a precise and constant force between the surface of a sheet of material and a transducer element, but it also provide reaction times that can allow for adjustment to the introduction of a sheet of material into the position between transducer element and lift wheel and/or variations in the surface of a sheet of material, in nearly real time to all but eliminate the bounce/recovery oscillations associated with prior art ultrasonic density detection systems. Consequently, the disclosed embodiments can obtain precise density measurements of an entire sheet of material without loss of data and with unprecedented accuracy unobtainable using prior art ultrasonic density detection systems.

In addition, in one embodiment, the magnetic force feedback actuator positioner can provide accurate displacement information for thickness measurement superior to prior art ultrasonic density detection systems by using current prior art transducer lever arm thickness/displacement sensors to detect the movement of prior art transducer lever arm vertical thickness measurement components.

In addition, in one embodiment, the magnetic force feedback actuator positioner utilizes a displacement sensor to detect the presence of a sheet of material to trigger the transmitting transducer element to begin operation. This internal measurement ability of the magnetic force feedback actuator positioner can accurately and rapidly trigger pulse transmission as a result of displacement without the use of mechanical or electromechanical switches. Therefore, using the disclosed embodiments, the reliability and efficiency of operation is greatly increased compared to prior art ultrasonic density detection systems that can be falsely triggered by trash on the conveyor line.

By maintaining a precise constant pressure/force on transducer elements, and therefore keeping the pressure/force of the transducer elements on the surface of sheet of material constant, the disclosed use of magnetic force feedback actuator positioner provides an accuracy and reliability of density measurements unobtainable using prior art ultrasonic density detection systems. This is accomplished by eliminating the relatively antiquated mechanical/pneumatic prior art pneumatic position system air bag and spring systems. This, in turn eliminates the prior art PSI and gauge errors inherent in prior art ultrasonic density detection systems and the resulting significant variance in density readings from actual density from pulse to pulse in the same sheet of material.

In addition, the disclosed use of magnetic force feedback actuator positioner provides for simple and precise force/pressure adjustments for various types of material making up sheets of material. In addition, the disclosed use of magnetic force feedback actuator positioner provides for the precise adjustment of applied pressure force to compensate for lift wheel eccentricity due to manufacturing imperfections and wear and tear resulting from the rebound force.

In addition, the disclosed use of magnetic force feedback actuator positioner eliminates the need for prior art transducer lever arm thickness/displacement sensors and prior art transducer lever arm vertical thickness measurement components. This results in a simpler, lighter, and less failure prone system that require less maintenance.

In addition, the disclosed use of magnetic force feedback actuator positioner eliminates the need for prior art sheet of material detector. This eliminates yet more components that need to be maintained, are subject to failure, and are subject to false indicators using prior art ultrasonic density detection systems.

As discussed in more detail below, the disclosed embodiments utilizing a magnetic force feedback actuator positioner are able to provide the precise, consistent, and accurate density readings now needed/required in many industries. In addition, the disclosed embodiments utilizing a magnetic force feedback actuator positioner have fewer parts and components than prior art ultrasonic density detection systems and are therefore less subject to failure, are lighter, and require less maintenance Consequently, the disclosed embodiments utilizing a magnetic force feedback actuator positioner are more efficient and effective, than prior art ultrasonic density detection systems and are less expensive to operate.

As a result of these and other disclosed features, which are discussed in more detail below, the disclosed embodiments address the short comings of the prior art.

BRIEF DESCRIPTION OF THE DRAWINGS

FIG. 2B is a simplified block diagram of a side view of the one illustrative example of the disclosed system for determining the density of a sheet of material of FIG. 2A showing several key components as a sheet of material, such as veneer, is passed through the disclosed system for determining the density of a sheet of material in accordance with one embodiment.

Figure 1A:
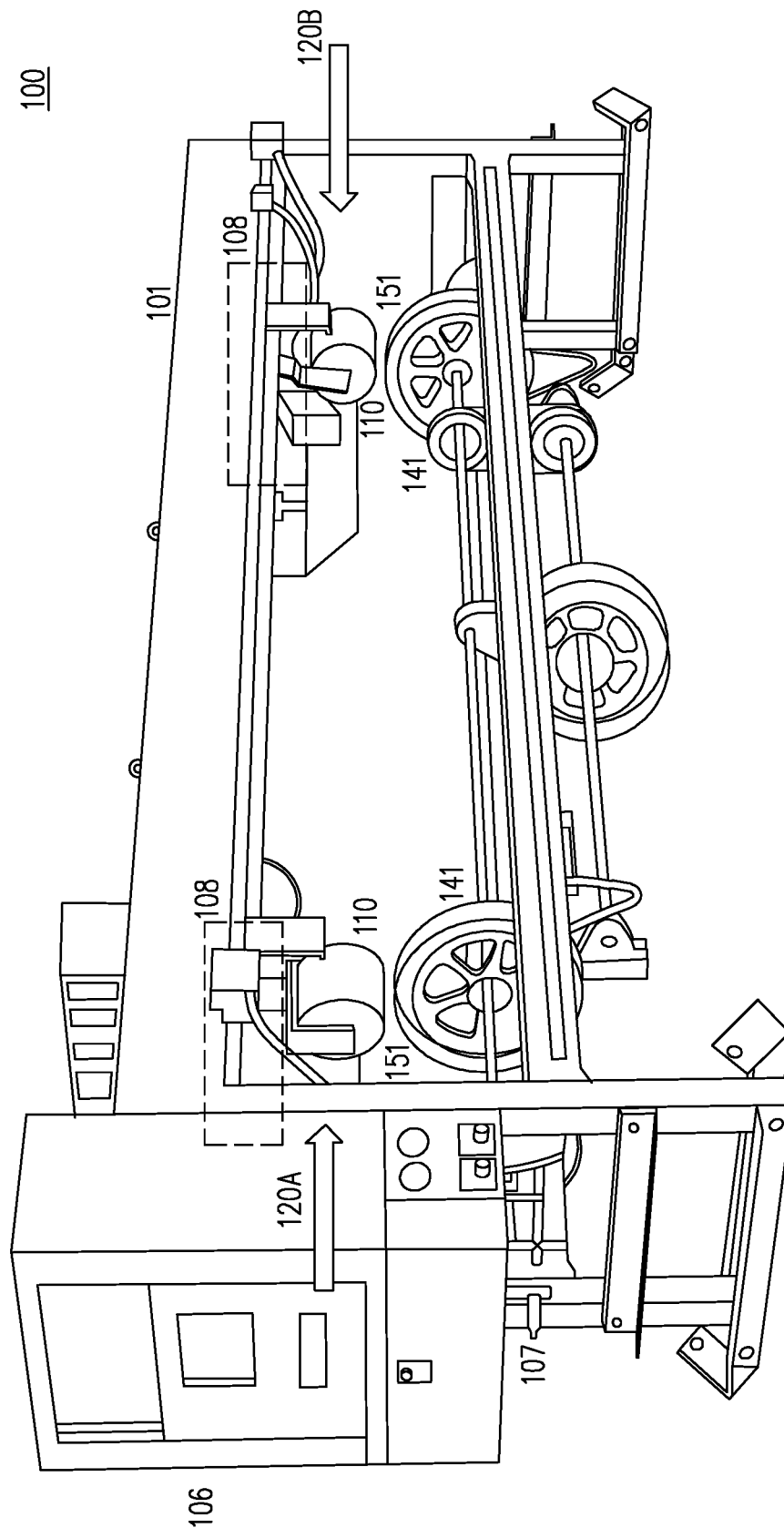
FIG. 1A is a photograph of a prior art ultrasonic density detection system showing several key components.
Figure 1B:
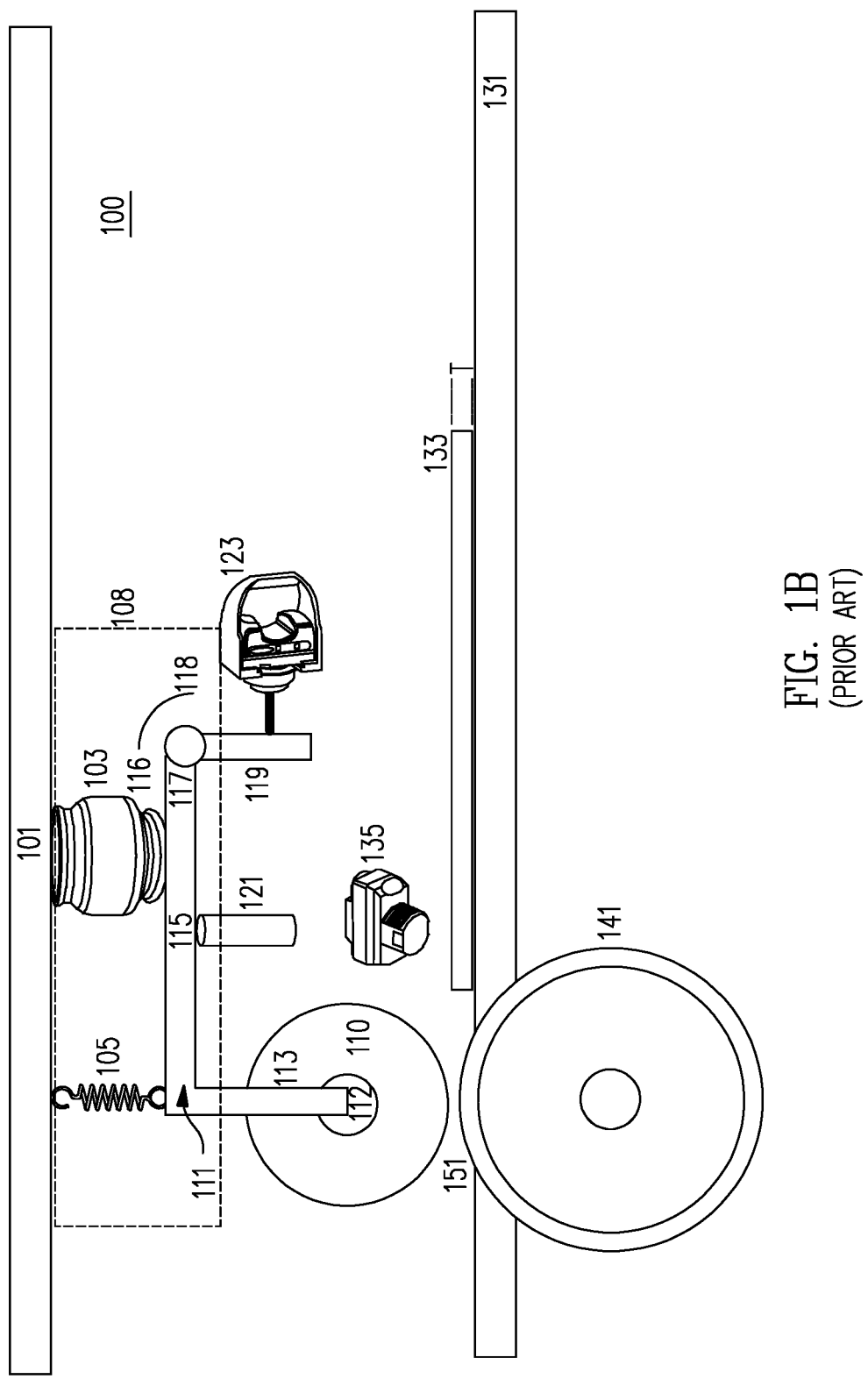
FIG. 1B is a simplified block diagram of a side view of the prior art ultrasonic density detection system of FIG. 1A showing several key components before sheet of material, such as veneer, is fed into prior art ultrasonic density detection system.
Figure 1C:
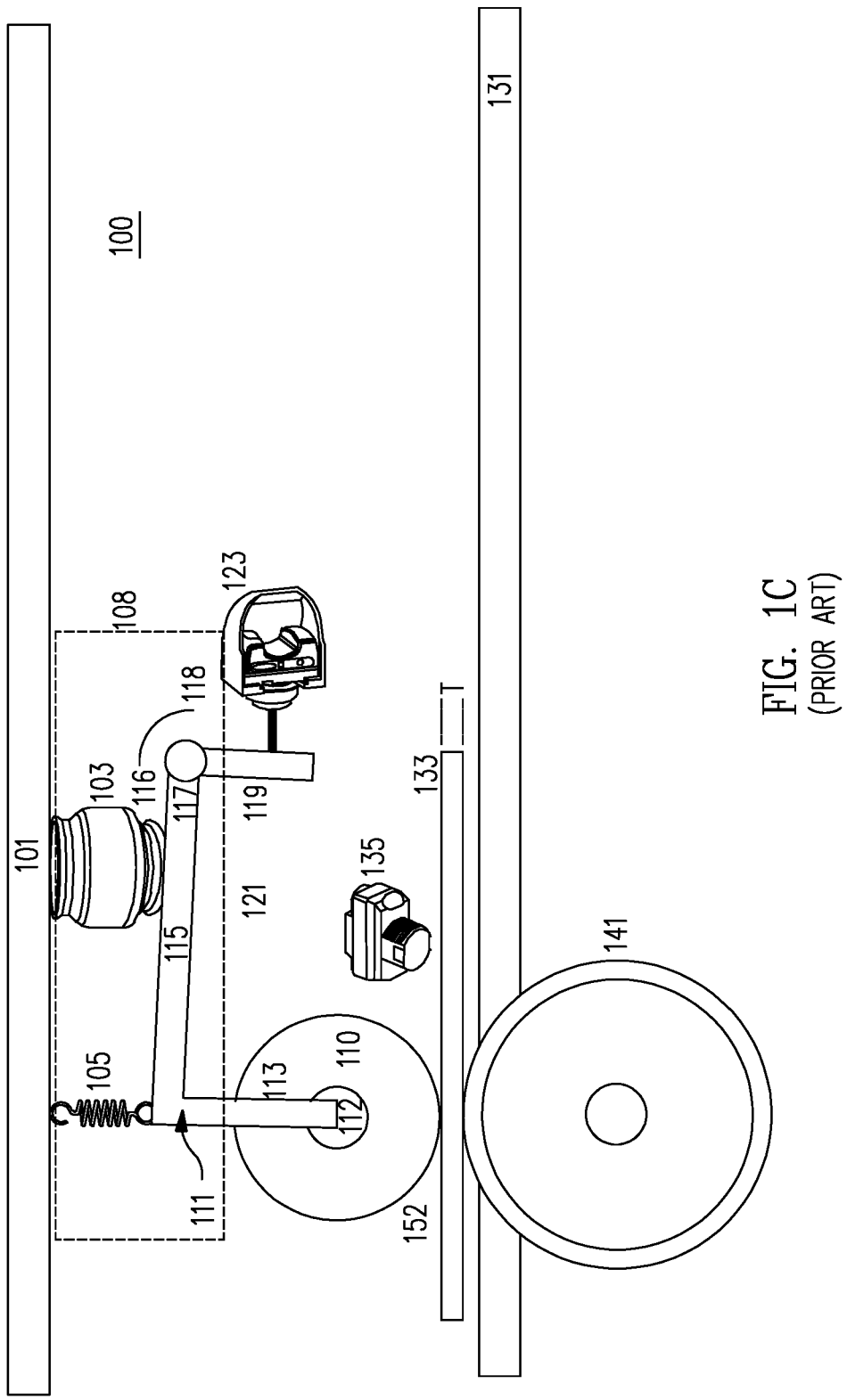
FIG. 1C is a simplified block diagram of a side view of the prior art ultrasonic density detection system of FIGS. 1A and 1B showing several key components as a sheet of material, such as veneer, passes through prior art ultrasonic density detection system.
Figure 1D:
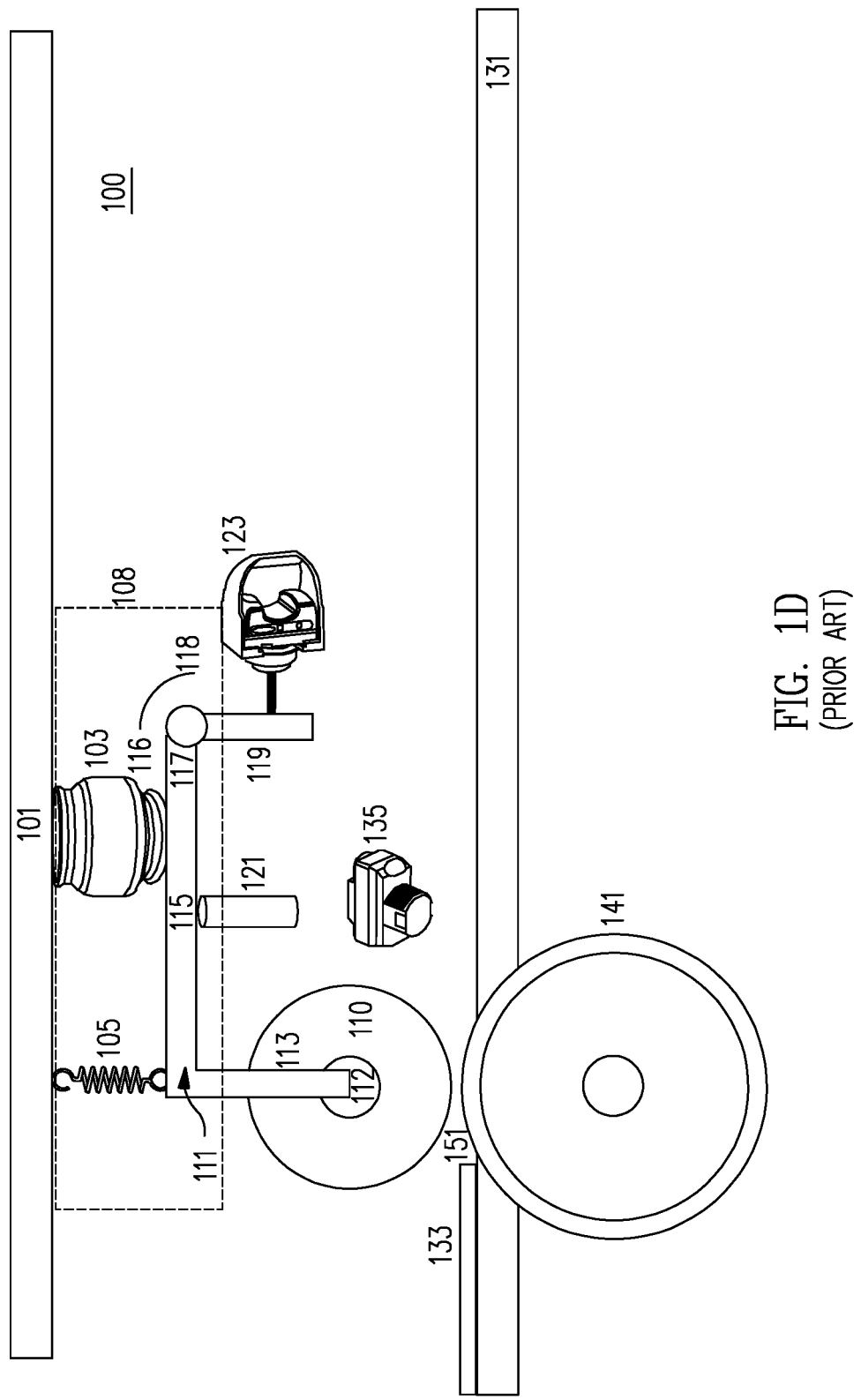
FIG. 1D is a simplified block diagram of a side view of the prior art ultrasonic density detection system of FIGS. 1A, 1B AND 1C after a sheet of material, such as veneer, passes through prior art ultrasonic density detection system.
Figure 1E:
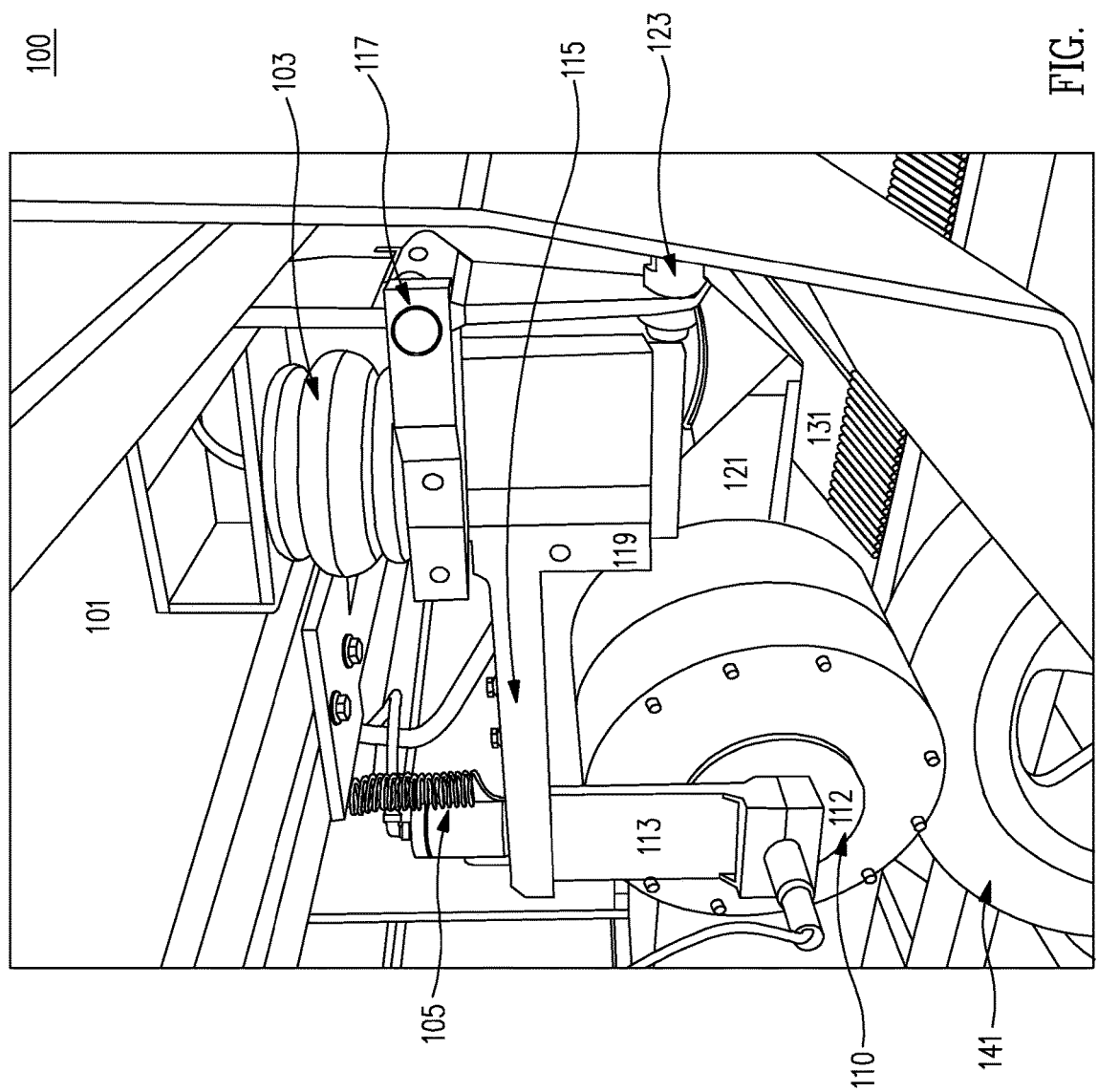
FIG. 1E is a line drawing of a prior art ultrasonic density detection system 100 showing several key components in more detail.
Figure 1G:
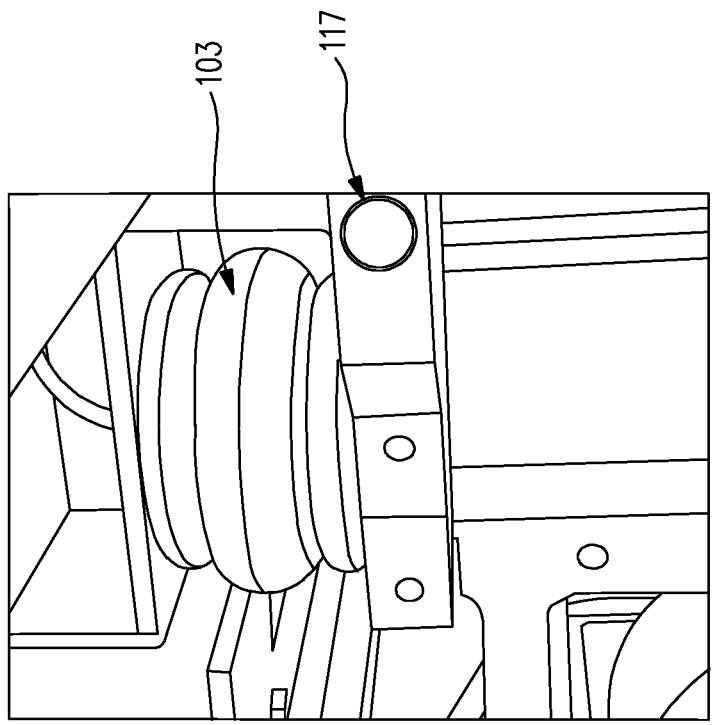
FIG. 1G is a line drawing showing prior art pneumatic position system air bag 103 of prior art ultrasonic density detection system 100 in more detail.
Figure 1F:
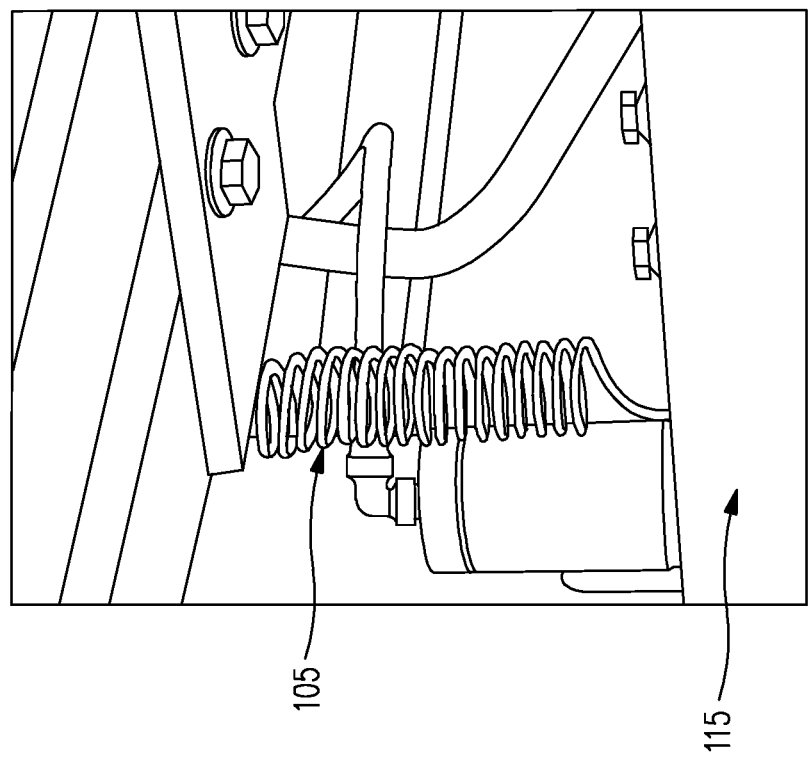
FIG. 1F is a line drawing showing counter balance spring 105 of prior art ultrasonic density detection system 100 in more detail.
Figure 1I:
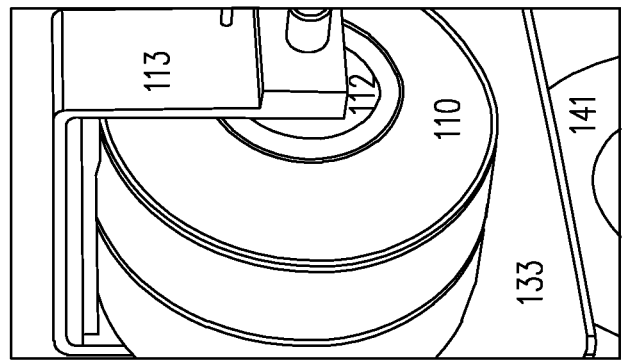
FIG. 1I is a line drawing of a transmitting transducer wheel/lift wheel receiver transducer wheel/lift wheel pair of the prior art ultrasonic density detection system of FIGS. 1A through 1G showing more detail before or after a sheet of material, such as veneer, passes through prior art ultrasonic density detection system as is also depicted in FIG. 1C.
Figure 1H:
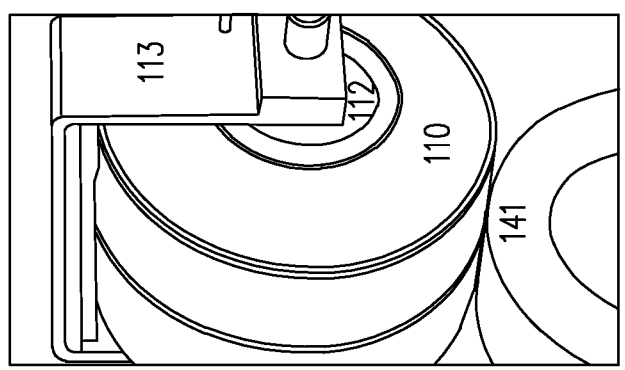
FIG. 1H is a line drawing of a transmitting transducer wheel/lift wheel receiver transducer wheel/lift wheel pair of the prior art ultrasonic density detection system of FIGS. 1A through 1G showing more detail before a sheet of material, such as veneer, is fed into prior art ultrasonic density detection system as is also depicted in FIGS. 1B and 1D.
Figure 1J:
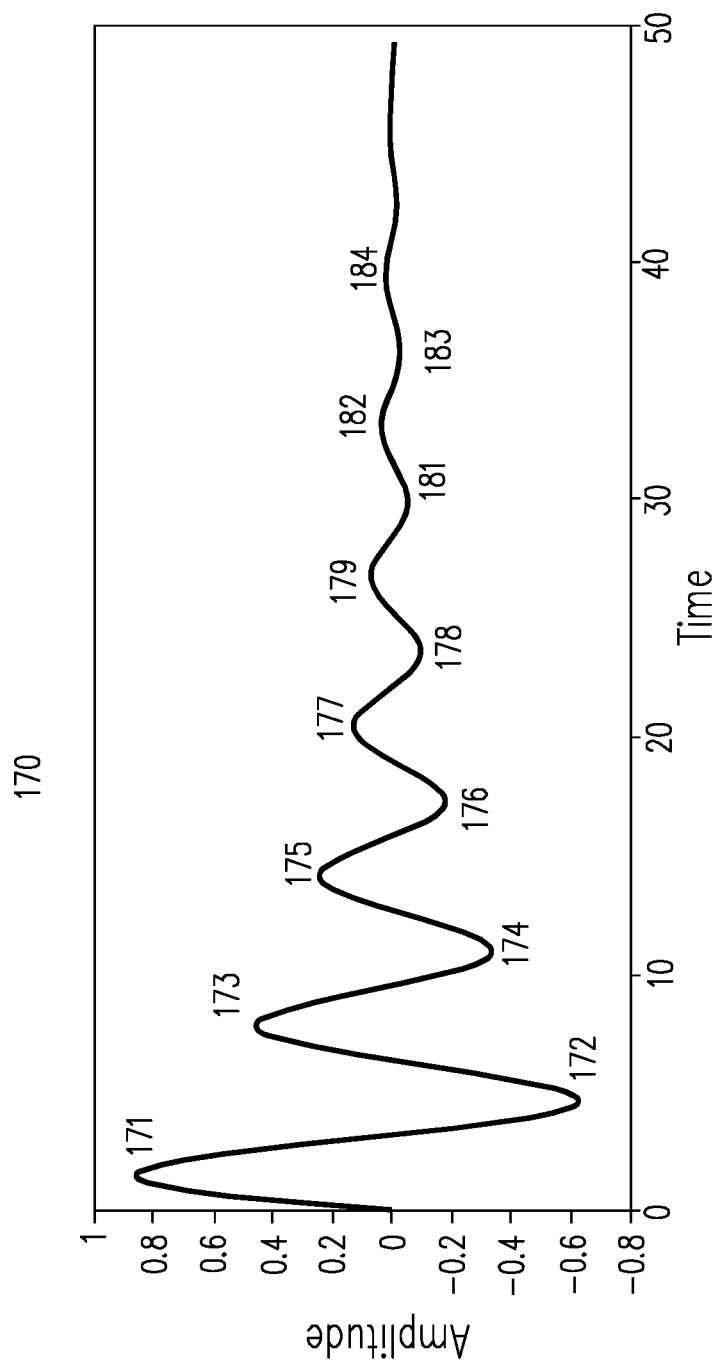
FIG. 1J shows a representation of the bounce/recovery time problem associated with prior art ultrasonic density detection systems.

Common reference numerals are used throughout the figures and the detailed description to indicate like elements. One skilled in the art will readily recognize that the above figures are merely illustrative examples and that other architectures, modes of operation, orders of operation, and elements/functions can be provided and implemented without departing from the characteristics and features of the invention, as set forth in the claims.

DETAILED DESCRIPTION

Embodiments will now be discussed with reference to the accompanying figures, which depict one or more exemplary embodiments. Embodiments may be implemented in many different forms and should not be construed as limited to the embodiments set forth herein, shown in the figures, or described below. Rather, these exemplary embodiments are provided to allow a complete disclosure that conveys the principles of the invention, as set forth in the claims, to those of skill in the art.

The disclosed embodiments utilize one or more magnetic force feedback actuator positioners to accurately maintain a constant selected pressure/force between transducer elements and the surface of a sheet of material as the sheet of material moves through the position between a transmitting transducer element and/or a receiver transducer element. Consequently, according to the disclosed embodiments, the antiquated mechanical/pneumatic springs/airbags of prior art ultrasonic density detection systems are replaced with a highly responsive magnetic force feedback actuator positioner.

The disclosed use of a magnetic force feedback actuator positioner provides not only for a method and system to maintain a precise and constant force between the surface of a sheet of material and a transducer element, but it also provide reaction times that can allow for adjustment to the introduction of a sheet of material into the position between transducer element and a lift element, and/or variations in the surface of a sheet of material, in nearly real time to all but eliminate the bounce/recovery oscillations associated with prior art ultrasonic density detection systems. Consequently, the disclosed embodiments can obtain precise density measurements of an entire sheet of material without loss of data and with unprecedented accuracy unobtainable using prior art ultrasonic density detection systems.

In addition, in one embodiment, the magnetic force feedback actuator positioner can provide accurate displacement information for thickness measurement superior to prior art ultrasonic density detection systems using current prior art transducer lever arm thickness/displacement sensors to detect the movement of prior art transducer lever arm vertical thickness measurement components.

In addition, in one embodiment, the magnetic force feedback actuator positioner utilizes a displacement sensor to detect the presence of a sheet of material to trigger the transmitting transducer element to begin operation. This internal measurement ability of the magnetic force feedback actuator positioner can accurately and rapidly trigger pulse transmission as a result of displacement without the use of prior art switching mechanisms. Therefore, using the disclosed embodiments, the reliability and efficiency of operation is greatly increased compared to prior art ultrasonic density detection systems that can be falsely triggered by trash on the conveyor line.

As discussed in more detail below, the disclosed embodiments utilizing a magnetic force feedback actuator positioner are able to provide the precise, consistent, and accurate density readings now needed/required in many industries. In addition, the disclosed embodiments utilizing a magnetic force feedback actuator positioner have fewer parts and components than prior art ultrasonic density detection systems and are therefore less subject to failure, are lighter, and require less maintenance Consequently, the disclosed embodiments utilizing a magnetic force feedback actuator positioner are more efficient and effective, than prior art ultrasonic density detection systems and are less expensive to operate.

Figure 2A:
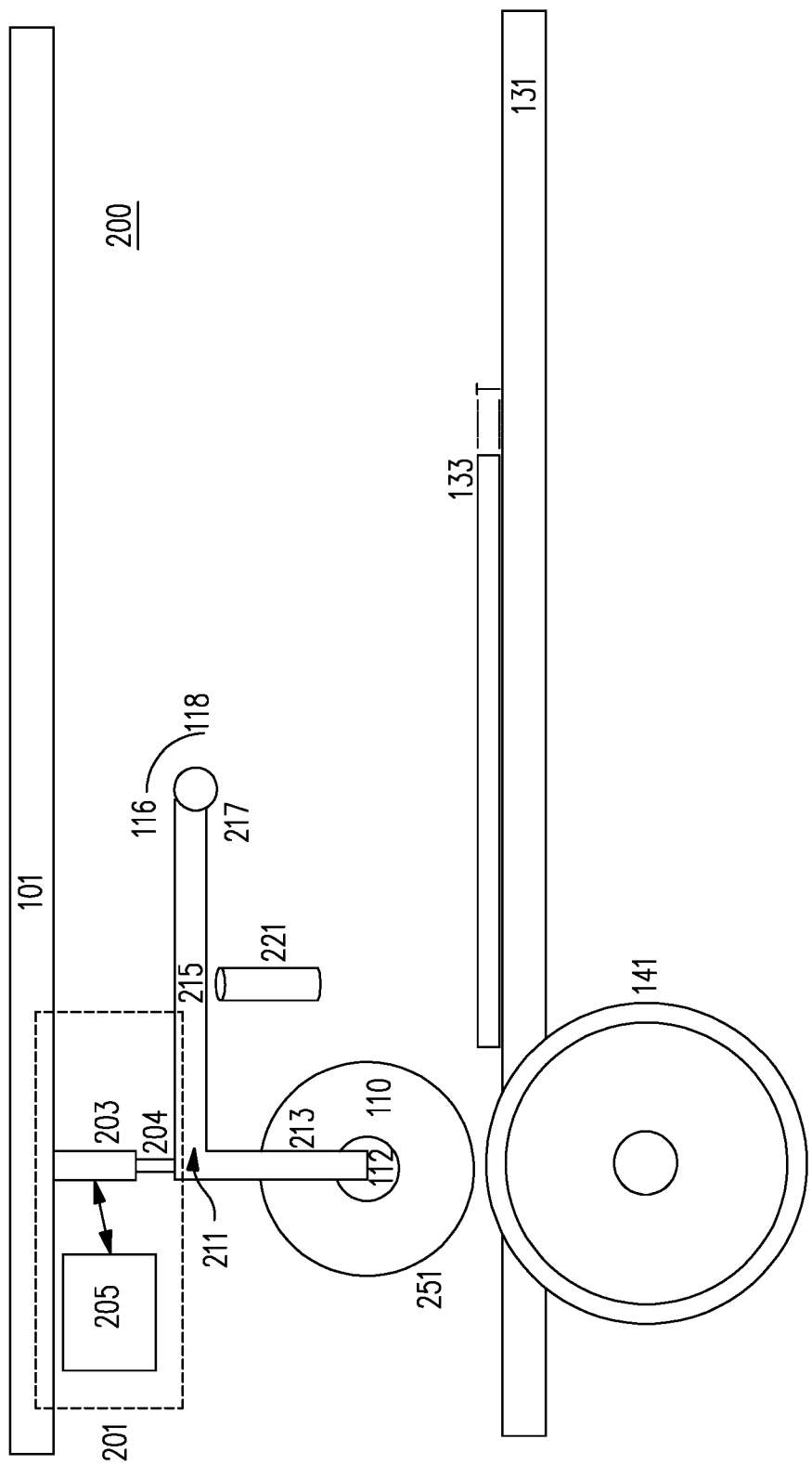
FIG. 2A is a simplified block diagram of a side view of one illustrative example of the disclosed system for determining the density of a sheet of material showing several key components before sheet of material, such as veneer, is fed into the disclosed system for determining the density of a sheet of material in accordance with one embodiment.

FIG. 2A is a simplified block diagram of a side view of one illustrative example of the disclosed system 200 for determining the density of a sheet of material showing several key components before a sheet of material 133, such as veneer, is fed into the disclosed system 200 for determining the density of a sheet of material in accordance with one embodiment.

FIG. 2B is a simplified block diagram of a side view of the one illustrative example of the disclosed system 200 for determining the density of a sheet of material of FIG. 2A showing several key components as a sheet of material 133, such as veneer, is fed into and passes through the disclosed system 200 for determining the density of a sheet of material in accordance with one embodiment.

Figure 2C:
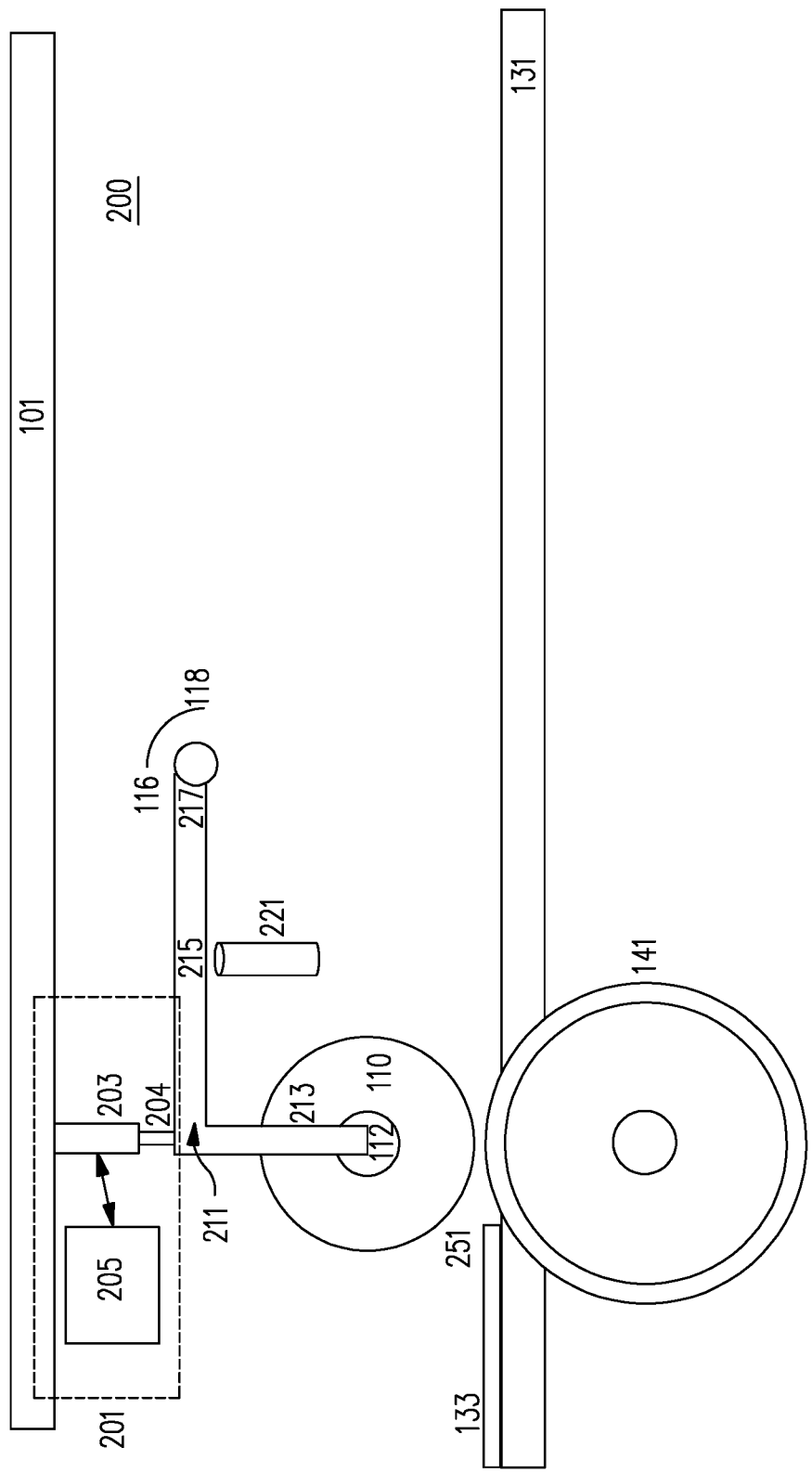
FIG. 2C is a simplified block diagram of a side view of the one illustrative example of the disclosed system for determining the density of a sheet of material of FIGS. 2A and 2B showing several key components after a sheet of material, such as veneer, exits the disclosed system for determining the density of a sheet of material in accordance with one embodiment.

FIG. 2C is a simplified block diagram of a side view of the one illustrative example of the disclosed system 200 for determining the density of a sheet of material of FIGS. 2A and 2B showing several key components after a sheet of material 133, such as veneer, exits the disclosed system 200 for determining the density of a sheet of material in accordance with one embodiment.

As seen in FIGS. 2A through 2C, the disclosed system 200 for determining the density of a sheet of material includes: support frame 101; magnetic force feedback actuator positioner system 201 including magnetic force feedback actuator positioner 203 and magnetic force feedback actuator positioner control system 205; transducer wheel 110; magnetic force feedback actuator positioner controlled lever arm 211 including transducer element support 213, lever arm horizontal component 215, and lever arm pivot point 217; lever arm stop 221; conveyor system 131; sheet of material 133; lift wheel 141; and gaps 251 and 252 (FIG. 2B) between transducer wheel 110 and lift wheel 141.

Referring to FIGS. 2A through 2C and FIGS. 1A through 1G together and comparing the disclosed system 200 for determining the density of a sheet of material with prior art ultrasonic density detection system 100, notably absent from the disclosed system 200 for determining the density of a sheet of material are: prior art pneumatic position system air bag 103, prior art counter balance spring 105, prior art transducer lever arm vertical thickness measurement component 119, prior art transducer lever arm thickness/displacement sensor 123, and prior art sheet of material detector 135. As discussed in more detail, not only does the removal of these elements result in less elements, less failures, less maintenance, and less weight of the disclosed system 200 for determining the density of a sheet of material compared to prior art ultrasonic density detection system 100, but it also provides for significantly more accurate density measurements and simplicity of operation.

In one embodiment, support frame 101 is typically made up of several beam and frame components. Typically, these components are made of stainless steel or a similarly solid, and heavy, material to provide support and a framework for the disclosed system 200 for determining the density of a sheet of material.

As seen in FIGS. 2A through 2C, magnetic force feedback actuator positioner 203 of magnetic force feedback actuator positioner system 201 is operatively coupled to prior art support frame 101 and lever arm horizontal component 215 of magnetic force feedback actuator positioner-controlled transducer lever arm 211.

Again, it is to be noted that, in one embodiment, prior art transducer lever arm vertical thickness measurement component 119 is not included in magnetic force feedback actuator positioner-controlled transducer lever arm 211. This alone represents a manufacturing and weight savings.

As also seen in FIGS. 2A through 2C, magnetic force feedback actuator positioner system 201 includes magnetic force feedback actuator positioner control system 205 electrically coupled to magnetic force feedback actuator positioner 203 for transmitting and receiving signals to and from magnetic force feedback actuator positioner 203 to control magnetic force feedback actuator positioner 203.

Again, referring to FIGS. 2A through 2C and FIGS. 1A through 1G together and comparing the disclosed system 200 for determining the density of a sheet of material with prior art ultrasonic density detection system 100, according to the disclosed embodiments, magnetic force feedback actuator positioner system 201 replaces prior art pneumatic position system air bag 103, prior art counter balance spring 105, prior art transducer lever arm vertical thickness measurement component 119, prior art transducer lever arm thickness/displacement sensor 123, and prior art sheet of material detector 135.

As discussed in more detail below, the purpose of magnetic force feedback actuator positioner system 201 is to provide a very precisely controlled constant pressure on lever arm horizontal component 215 of magnetic force feedback actuator positioner-controlled transducer lever arm 211 which, in turn, provides a constant pressure on transducer element support 213 of magnetic force feedback actuator positioner controlled transducer lever arm 211 and transducer wheel 110.

As also discussed in more detail below, the disclosed use of magnetic force feedback actuator positioner system 201 mitigates and/or eliminates the numerous, and significant, limitations on the ability of prior art ultrasonic density detection system 100 to accurately provide the theoretically constant pressure/force on transducer lever arm horizontal component and transducer wheel 110. Therefore, the disclosed use of magnetic force feedback actuator positioner system 201 provides for density measurement accuracy unobtainable using prior art ultrasonic density detection systems, such as prior art ultrasonic density detection system 100.

As also seen in FIGS. 2A through 2C, magnetic force feedback actuator positioner-controlled transducer lever arm 211 is movably, i.e., rotationally, operatively coupled to lever arm pivot point 217 such that magnetic force feedback actuator positioner-controlled transducer lever arm 211 can rotate/pivot in either direction 116 or 118 about lever arm pivot point 217. As seen in FIGS. 2A through 2C, transducer wheel 110 is supported by transducer element support 213 of magnetic force feedback actuator positioner controlled transducer lever arm 211 at rotating center hub 112.

Of note, in the one illustrative example of one embodiment of FIGS. 2A through 2C, transducer wheel 110 is used as the housing enclosure of a transducer element, i.e., a transmitting or receiving transducer element. However, transducer wheel 110 FIGS. 2A through 2C is merely representative of various types of transducer elements and/or transducer element housings. In other embodiments, one or more of the transducer elements, i.e., a transmitting or receiving transducer elements, can be provided with or without a housing and in some cases n a housing that is not a transducer wheel. Consequently, the specific illustrative example of one embodiment of FIGS. 2A through 2C is not to be construed as limiting the inventions as set forth in the claims.

Also seen in FIGS. 2A through 2C is lever arm stop 221. Lever arm stop 221 prevents magnetic force feedback actuator positioner controlled transducer lever arm 211 from pivoting too far in direction 116 such that transducer wheel 110 comes in contact with lift wheel 141 when there is no sheet of material 133 positioned between transducer wheel 110 and lift wheel 141 (as shown in FIG. 2A). Consequently, lever arm stop 221 ensures a minimal home gap 251 between transducer wheel 110 and lift wheel 141. Lever arm stop 221 is typically made of urethane or a similar material.

FIGS. 2A through 2C also show sheet of material 133 being conveyed to, and passing through, the disclosed system 200 for determining the density of a sheet of material by conveyor system 131. In various cases, sheet of material 133 is a sheet of veneer, a sheet of any wood product, or a sheet of any material that is to be analyzed by the disclosed system 200 for determining the density of a sheet of material. In various cases, conveyor system 131 is any standard conveyor system such as a traditional conveyor belt.

Referring to FIGS. 2A through 2C, in operation, sheet of material 133 moves along conveyor system 131 to, and through, a density analysis station including the disclosed system 200 for determining the density of a sheet of material. As seen in FIG. 2A, in one embodiment, lever arm stop 221 prevents magnetic force feedback actuator positioner-controlled transducer lever arm 211 from pivoting too far in direction 116 such that transducer wheel 110 comes in contact with lift wheel 141 when there is no sheet of material 133 positioned between transducer wheel 110 and lift wheel 141 (as shown in FIG. 2A).

Consequently, in one embodiment, lever arm stop 221 ensures a minimal, or equilibrium, home gap 251 between transducer wheel 110 and lift wheel 141. In addition, in one embodiment, magnetic force feedback actuator positioner-controlled transducer lever arm 211 and transducer wheel 110 are in the neutral home position at this time (FIGS. 2A and 2C).

Of note, the one illustrative example of one embodiment of FIGS. 2A through 2C includes lift wheel 141, and sheet of material 133 is positioned between lift wheel 141 and a transducer element, i.e., a transmitting or receiving transducer element, such as represented by transducer wheel 110. However, lift wheel 141 of FIGS. 2A through 2C is merely representative of various mechanisms through which sheet of material passes such that sheet of material 133 is positioned between these mechanisms and a transducer element, such as transducer wheel 110. In addition, in some embodiments, lift wheel 141 is not present, and sheet of material 133 is positioned between a flat surface and a transducer element, such as transducer wheel 110. Consequently, the specific illustrative example of one embodiment of FIGS. 2A through 2C is not to be construed as limiting the inventions as set forth in the claims.

In one embodiment, magnetic force feedback actuator positioner 203 of magnetic force feedback actuator positioner system 201 maintains home, also known as a neutral or equilibrium, position as commanded by magnetic force feedback actuator positioner control system 205 of magnetic force feedback actuator positioner system 201. In one embodiment, the home position the gap 251 between the transducer wheel 110 and the lift wheel 141 is approximately one tenth of an inch. While in this home position, actuator element 204 of magnetic force feedback actuator positioner 203 can be commanded by magnetic force feedback actuator positioner control system 205 of magnetic force feedback actuator positioner system 201 to present only slight resistance to rising as sheets of material 133 enter the gap 251/252 between the transducer wheel 110 and the lift wheel 141. This fact, and the fact magnetic force feedback actuator positioner control system 205 of magnetic force feedback actuator positioner system 201 can react extremely quickly to adjust the extension of actuator element 204 of magnetic force feedback actuator positioner 203 (on the order of Kilo-Hertz reaction time), means that the recovery/bounce oscillation issues associated with prior art systems is significantly mitigated and/or virtually eliminated.

In one embodiment, then the lift of actuator element 204 of magnetic force feedback actuator positioner 203 is compressed by the entry of sheet of material 133 into the gap 252 between the transducer wheel 110 and the lift wheel 141 is detected, using magnetic force feedback actuator positioner system 201, actuator element 204 of magnetic force feedback actuator positioner 203 of provides a very precisely controlled constant pressure on lever arm horizontal component 215 of magnetic force feedback actuator positioner-controlled transducer lever arm 211 which, in turn, provides a constant pressure on transducer element support 213 of magnetic force feedback actuator positioner-controlled transducer lever arm 211 and transducer wheel 110.

In one embodiment, once the sheet of material 133 passes through the gap 252 between the transducer wheel 110 and the lift wheel 141, gap 252 is reduced back to the home gap 251 and the home command will be executed awaiting the next cycle.

Thus, using the disclosed magnetic force feedback actuator positioner, the far less precise and more complicated use of prior art transducer lever arm vertical thickness measurement component 119 and prior art transducer lever arm thickness/displacement sensor 123 to make offset thickness measurements is avoided.

Referring again to FIGS. 2A through 2C, as seen in FIG. 2B, as sheet of material 133 moves through the position between transducer wheel 110 and lift wheel 141, transducer wheel 110 is lifted up so that the gap 252 between transducer wheel 110 and lift wheel 141 of FIG. 2B is greater that gap 251 of FIG. 2C, typically by a distance equal to the thickness T of sheet of material 133. This, in turn, causes magnetic force feedback actuator positioner controlled transducer lever arm 211 to pivot in direction 118 around lever arm pivot point 217 as transducer wheel 110 is lifted up.

In one embodiment, as sheet of material 133 moves between lift wheel 141 and a transducer element, i.e., a transmitting or receiving transducer element, such as represented by transducer wheel 110, actuator element 204 of magnetic force feedback actuator positioner 203 is compressed (see FIG. 2B) by a precisely measurable distance equal to the thickness of sheet of material 133. In one embodiment, magnetic force feedback actuator positioner control system 205 then records this compression distance of actuator element 204 as the thickness T of sheet 133. Thus, using the disclosed magnetic force feedback actuator positioner, the far less precise and more complicated use of prior art transducer lever arm vertical thickness measurement component 119 and prior art transducer lever arm thickness/displacement sensor 123 to make offset thickness measurements is avoided.

In one embodiment, the disclosed system 200 for determining the density of a sheet of material typically includes a minimum of two transducer wheels, and two lift wheels in pairs of transmitting transducer wheel 110/lift wheel 141 and pairs of receiving transducer wheel 110/lift wheel 141. This is similar to the basic configuration shown in FIG. 1A with magnetic force feedback actuator positioner system 201 replacing prior art pneumatic position systems 108. As the sheet of material 133 is conveyed by the conveyor system 131 between the transmitting transducer wheel 110 and lift wheel 141 and the receiving transducer wheel 110 and lift wheel 141 a first portion of the sheet of material 133 is in contact with the transmitting transducer wheel 110 and lift wheel 141 at the same time a second portion of the sheet of material is in contact with the receiving transducer wheel 110 and lift wheel 141. As noted above, the transmitting transducer wheel 110 and lift wheel 141 pair and the receiving transducer wheel 110 and lift wheel 141 are typically separated by a precisely defined distance, often around six feet. However, the accurate measurement of the distance is more important than the distance chosen.

In one embodiment, as sheet of material 133 moves between transmitting lift wheel 141 and a transducer element, i.e., a transmitting or receiving transducer element, such as represented by transducer wheel 110, actuator element 204 of magnetic force feedback actuator positioner 203 is compressed (see FIG. 2B) by a precisely measurable distance equal to the thickness of sheet of material 133, typically 0.125-0.166 inch for veneer. In one embodiment, magnetic force feedback actuator positioner control system 205 then records this compression distance of actuator element 204 as the thickness T of sheet 133. In one embodiment, this compression distance of actuator element 204, and the thickness T of sheet 133, is measure continuously via magnetic force feedback actuator positioner control system 205 and an internal position indication inside magnetic force feedback actuator positioner 203.

Once the first portion of the sheet of material 133 is between the transmitting transducer wheel 110 and lift wheel 141 and, at the same time, the second portion of the sheet of material 133 is between with the receiving transducer wheel 110 and lift wheel 141, the transmitting transducer element, i.e., in transducer wheel 110 or transducer wheel 110 emits an ultrasonic signal (typically in pulses). By separating the transmitting transducer wheel 110 and receiving transducer wheel 110, by the precisely defined fixed distance, an ultrasonic pulse transmitted into the first portion of the sheet of material 133 by the transmitting transducer element, i.e., in transmitting transducer wheel 110, then travels through the sheet of material and can be received by the receiving transducer element, i.e., in the receiving transducer wheel 110 at the second portion of the sheet of material 133 by passing through the sheet of material 133 between the transmitting transducer element and the receiving transducer element.

As noted above, in the one illustrative example of one embodiment of FIGS. 2A through 2C, transducer wheel 110 is used as the housing enclosure of a transducer element, i.e., a transmitting or receiving transducer element. However, transducer wheel 110 FIGS. 2A through 2C is merely representative of various types of transducer elements and/or transducer element housings. In other embodiments, one or more of the transducer elements, i.e., a transmitting or receiving transducer elements, can be provided with or without a housing and in some cases n a housing that is not a transducer wheel. Consequently, the specific illustrative example of one embodiment of FIGS. 2A through 2C is not to be construed as limiting the inventions as set forth in the claims.

Since the distance between the transmitting transducer element, i.e., in a transmitting transducer wheel 110, and receiving transducer element, i.e., in receiving transducer wheel 110 is known, the density of the sheet of material 133 can be determined by measuring the time it takes the ultrasonic pulse to travel from the transmitting transducer element, i.e., transmitting transducer wheel 110, through the known distance in the sheet of material 133, to the receiving transducer element, i.e., receiving transducer wheel 110. The density of the sheet of material 133 can then be determined based on the pulse travel time with shorter travel times generally indicating higher densities and longer travel times generally indicating lower densities. The correlation of pulse travel time to density will vary from material to material making up the sheet of material 133.

As the sheet of material 133 moves through the disclosed system 200 for determining the density of a sheet of material and the position between the transmitting transducer wheel 110/lift wheel 141, and the receiving transducer wheel 110/lift wheel 141, multiple density readings are captured at multiple locations along the sheet of material 133. A density reading taken every one to six inches along the sheet of material 133 is common. However, this distance is typically determined by the speed at which the sheet of material 133 is conveyed by conveyor system 131 or the time interval between transmitted pulse, or both, and therefore can be any distance desired.

As also noted above, the one illustrative example of one embodiment of FIGS. 2A through 2C includes lift wheel 141, and sheet of material 133 is positioned between lift wheel 141 and a transducer element, i.e., a transmitting or receiving transducer element, such as represented by transducer wheel 110. However, lift wheel 141 of FIGS. 2A through 2C is merely representative of various mechanisms through which sheet of material passes such that sheet of material 133 is positioned between these mechanisms and a transducer element, such as transducer wheel 110. In addition, in some embodiments, lift wheel 141 is not present, and sheet of material 133 is positioned between a flat surface and a transducer element, such as transducer wheel 110. Consequently, the specific illustrative example of one embodiment of FIGS. 2A through 2C is not to be construed as limiting the inventions as set forth in the claims.

As also noted above, in the one illustrative example of one embodiment of FIGS. 2A through 2C, transducer wheel 110 is used as the housing enclosure of a transducer element, i.e., a transmitting or receiving transducer element. However, transducer wheel 110 FIGS. 2A through 2C is merely representative of various types of transducer elements and/or transducer element housings. In other embodiments, one or more of the transducer elements, i.e., a transmitting or receiving transducer elements, can be provided with or without a housing and in some cases n a housing that is not a transducer wheel. Consequently, the specific illustrative example of one embodiment of FIGS. 2A through 2C is not to be construed as limiting the inventions as set forth in the claims.

Once the density of the sheet of material 133 is known, this can be used to determine a relative strength of the sheet of material 133, with higher densities generally equating to higher strength and lower densities generally equating to lower strength. The correlation of the sheet of material density to the sheet of material strength will vary from material to material making up the sheet of material 133

Referring to FIG. 2C, once the sheet of material 133 passes through the position between the transmitting transducer wheel 110 and lift wheel 141, and the receiving transducer wheel 110 and lift wheel 141, the disclosed system 200 for determining the density of a sheet of material returns to the starting/neutral positions of FIG. 2A. Consequently, lever arm stop 221 again prevents magnetic force feedback actuator positioner controlled transducer lever arm 211 from pivoting too far in direction 116 such that transducer wheel 110 comes in contact with lift wheel 141 when there is no sheet of material 133 positioned between transducer wheel 110 and lift wheel 141.

Consequently, lever arm stop 221 ensures a return to the minimal home gap 251 between transducer wheel 110 and lift wheel 141. In addition, magnetic force feedback actuator positioner-controlled transducer lever arm 211 and transducer wheel 110 are in the neutral/home position.

It is again important to note that the accuracy and reliability of density measurements taken using the disclosed system 200 for determining the density of a sheet of material is almost entirely dependent on keeping a constant pressure on transducer wheel 110, and therefore keeping the pressure/force of transducer wheel 110 on the surface of sheet of material constant. Any variation in this pressure/force will result in less accurate density readings, with larger variations resulting in larger inaccuracies. Using the disclosed system 200 for determining the density of a sheet of material this is accomplished using state of the art electronics in the form of magnetic force feedback actuator positioner system 201, including and magnetic force feedback actuator positioner 203 and magnetic force feedback actuator positioner control system 205.

As noted above, the purpose magnetic force feedback actuator positioner system 201 is to provide a very precisely controlled constant pressure on lever arm horizontal component 215 of magnetic force feedback actuator positioner-controlled transducer lever arm 211 which, in turn, provides a constant pressure on transducer element support 213 of magnetic force feedback actuator positioner-controlled transducer lever arm 211 and transducer wheel 110.

As also noted above, the disclosed use of magnetic force feedback actuator positioner system 201 mitigates and/or eliminates the numerous, and significant, limitations on the ability of prior art ultrasonic density detection system 100 to accurately provide the theoretically constant pressure/force on transducer lever arm horizontal component and transducer wheel 110. Therefore, the disclosed use of magnetic force feedback actuator positioner system 201 provides for density measurement accuracy unobtainable using prior art ultrasonic density detection systems, such as prior art ultrasonic density detection system 100.

In various embodiments, magnetic force feedback actuator positioner system 201 and magnetic force feedback actuator positioner 203 can be any of several magnetic force feedback actuator positioners and systems known in the art, and that are commercially available from several manufactures.

In other embodiments, magnetic force feedback actuator positioner system 201 and magnetic force feedback actuator positioner 203 can be any magnetic force feedback actuator positioner or system as discussed herein, known/available at the time of filing, and/or a developed/made available after the time of filing capable of providing and maintaining a very precisely controlled constant pressure on lever arm horizontal component 215 of magnetic force feedback actuator positioner-controlled transducer lever arm 211 which, in turn, provides a constant pressure on transducer element support 213 of magnetic force feedback actuator positioner-controlled transducer lever arm 211 and transducer wheel 110.

Figure 3A:
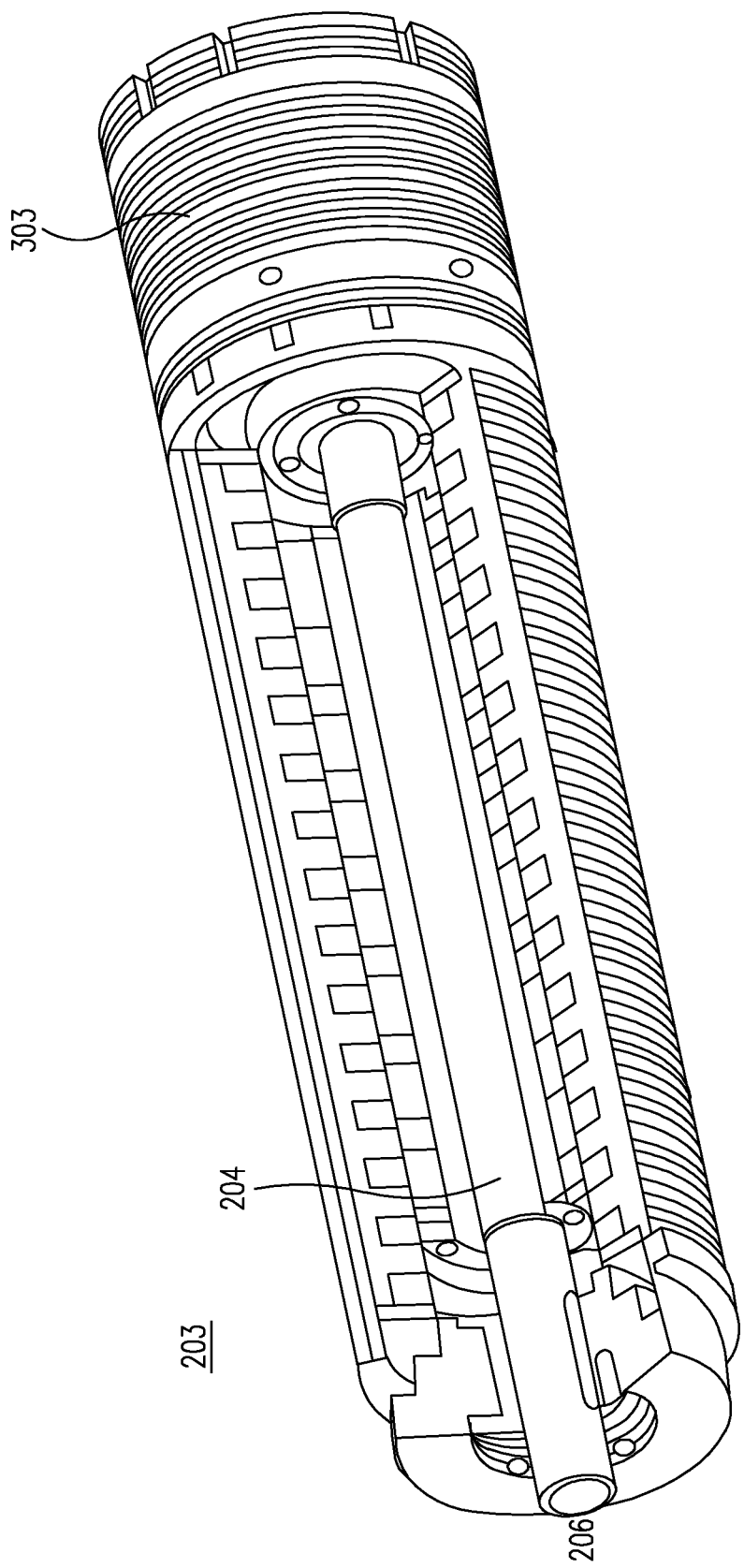
FIG. 3A shows a cut away view of one illustrative example of a magnetic force feedback actuator positioner that can be used with one illustrative example of the disclosed system for determining the density of a sheet of material.

FIG. 3A shows a cut away view of one illustrative example of a one magnetic force feedback actuator positioner 203 that can be used with one illustrative example of the disclosed system 200 for determining the density of a sheet of material. Referring to FIGS. 2A through 2C and FIG. 3A, as seen in FIG. 3A, magnetic force feedback actuator positioner 203 includes actuator element 204, actuator element end 206, and actuator housing 303.

Figure 3B:
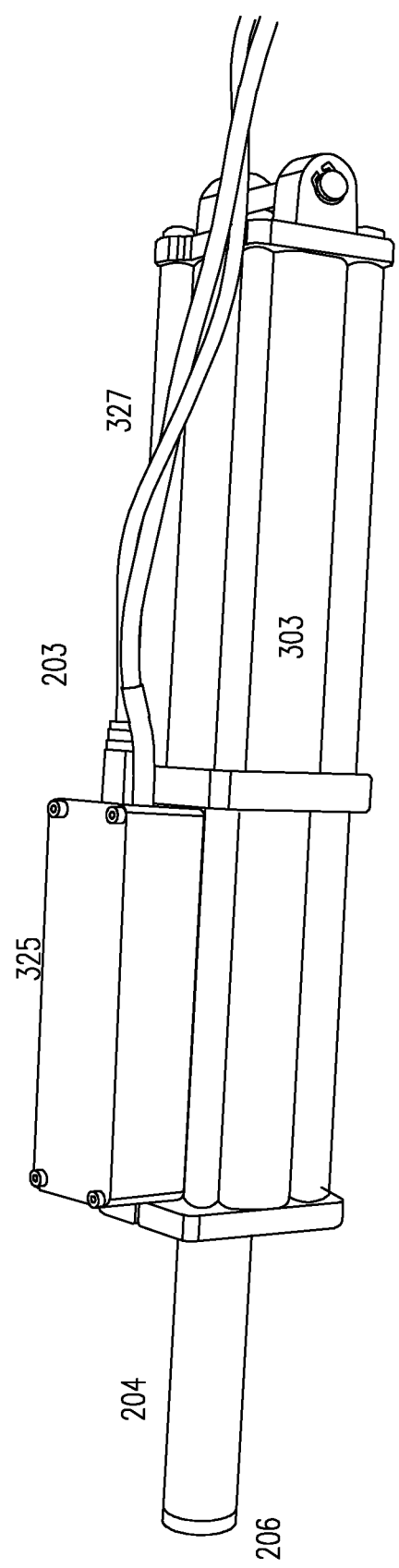
FIG. 3B shows one illustrative example of a currently available magnetic force feedback actuator positioner that can be used with one illustrative example of the disclosed system for determining the density of a sheet of material.

FIG. 3B shows one illustrative example of a currently available magnetic force feedback actuator positioner 203 that can be used with one illustrative example of the disclosed system 200 for determining the density of a sheet of material. Referring to FIGS. 2A through 2C and FIG. 3B, as seen in FIG. 3B, magnetic force feedback actuator positioner 203 includes actuator element 204, actuator element end 206, actuator housing 303, control input module 325 for receiving and sending signals to magnetic force feedback actuator positioner control system 205, and control wires 327 for transmitting signals between force feedback actuator positioner control system 202 and magnetic force feedback actuator positioner 203.

Figure 3C:
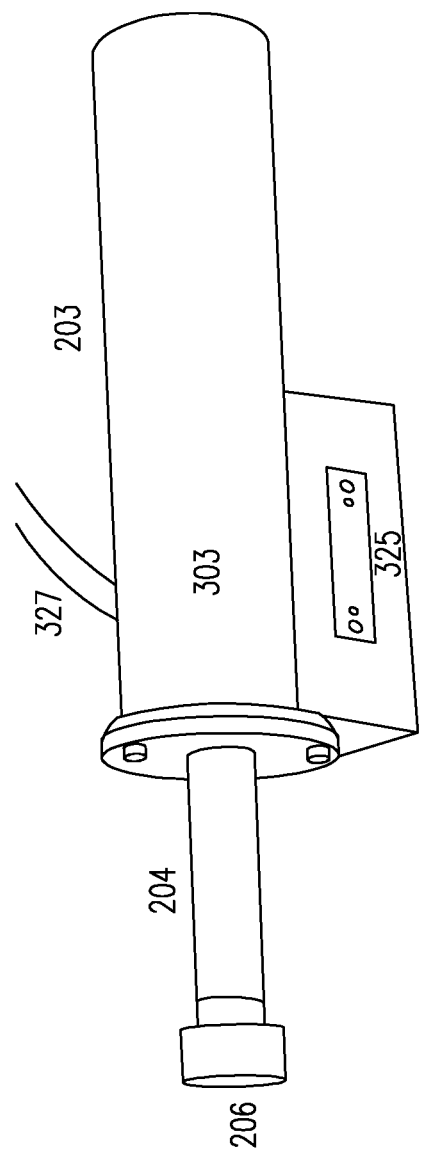
FIG. 3C shows another illustrative example of a currently available magnetic force feedback actuator positioner that can be used with one illustrative example of the disclosed system for determining the density of a sheet of material.

FIG. 3C shows one illustrative example of a currently available magnetic force feedback actuator positioner 203 that can be used with one illustrative example of the disclosed system 200 for determining the density of a sheet of material. Referring to FIGS. 2A through 2C and FIG. 3C, as seen in FIG. 3C, magnetic force feedback actuator positioner 203 includes actuator element 204, actuator element end 206, actuator housing 303, control input module 325 for receiving and sending signals to magnetic force feedback actuator positioner control system 205, and control wires 327 for between force feedback actuator positioner control system 202 and magnetic force feedback actuator positioner 203.

Figure 3D:
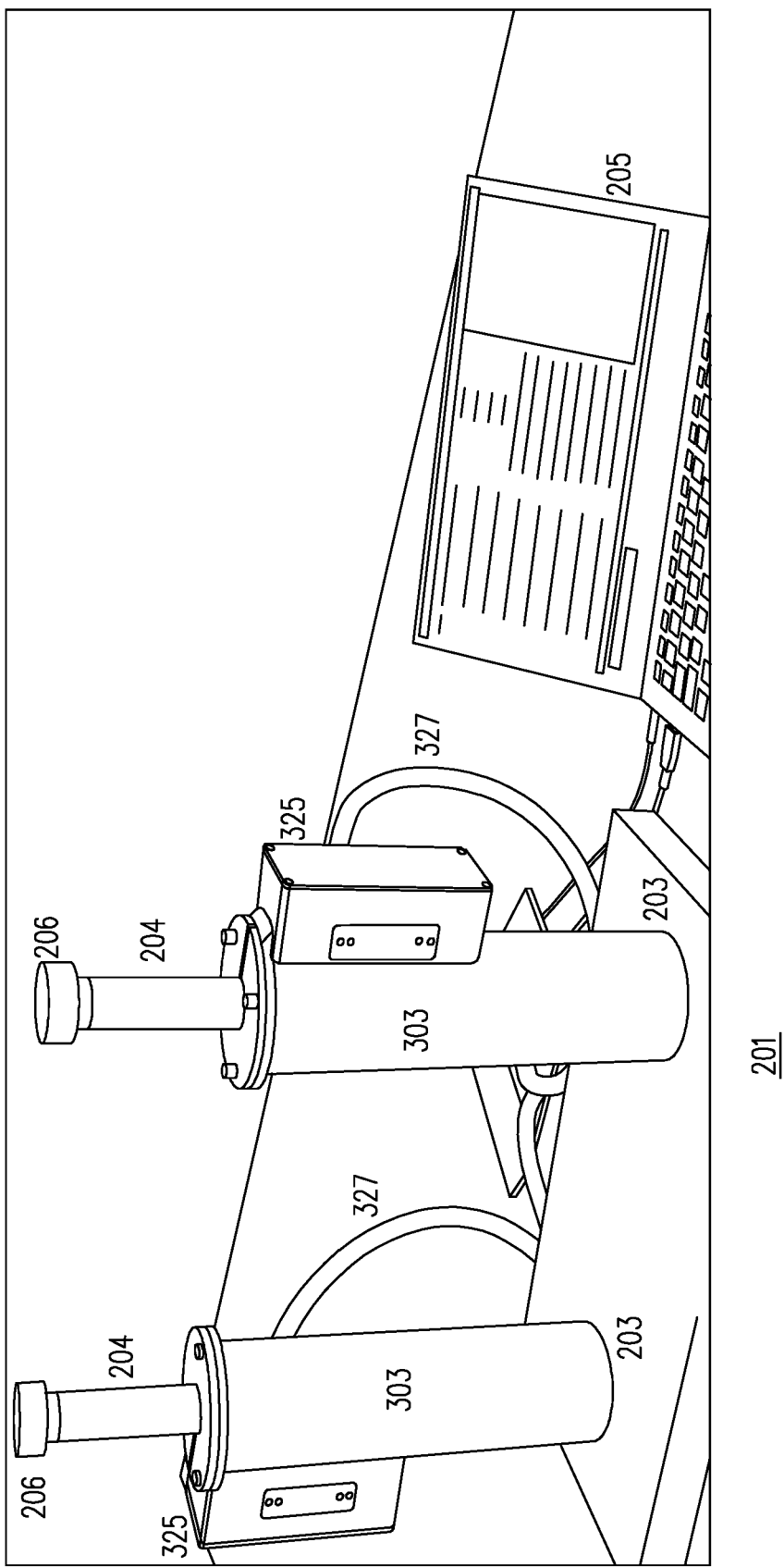
FIG. 3D shows an illustrative example of two currently available magnetic force feedback actuator positioners that can be used in tandem with one illustrative example of the disclosed system for determining the density of a sheet of material.

FIG. 3D shows one illustrative example of two currently available magnetic force feedback actuator positioners 203 that can be used with one illustrative example of the disclosed system 200 for determining the density of a sheet of material. Referring to FIGS. 2A through 2C and FIG. 3D, as seen in FIG. 3D, each of magnetic force feedback actuator positioners 203 includes actuator element 204, actuator element end 206, actuator housing 303, control input module 325 for receiving and sending signals to magnetic force feedback actuator positioner control system 205, and control wires 327 for transmitting signals between magnetic force feedback actuator positioner between force feedback actuator positioner control system 205 and magnetic force feedback actuator positioner 203.

In some embodiments a magnetic force feedback actuator positioner system 201 includes a magnetic force feedback actuator positioner 203 that uses generated magnetic fields produced by electromagnetic coils in the magnetic force feedback actuator positioner housing 303 to impart Lorentz force onto permanent magnets contained within actuator element 204. This, in turn causes actuator element 204 to move linearly in and out of magnetic force feedback actuator positioner housing 303 and to apply a desired selected force at actuator element end 206. This particular design contains just a single moving part, i.e., actuator element 204. Therefore, failure and maintenance problems are significantly reduced.

In addition, in some embodiments, magnetic force feedback actuator positioner system 201 and magnetic force feedback actuator positioner 203 operate in a forced feedback loop control mode whereby the magnetic force feedback actuator positioner system 201 includes a magnetic force feedback actuator positioner 203 that senses force output at actuator element end 206 and thus can feel detect/identify when a force or force change is imparted onto actuator element end 206. In some embodiments, this forced feedback loop control can react to a change in force in less than one millisecond. This allows magnetic force feedback actuator positioner system 201 and magnetic force feedback actuator positioner 203 to respond to changes in forces, or other inputs, nearly instantaneously. In addition, the inherent low friction contactless characteristics of magnetic force feedback actuator positioner 203 permit the resolution of that response to be on the scale of milligrams. This allows magnetic force feedback actuator positioner system 201 and magnetic force feedback actuator positioner 203 to be commanded by magnetic force feedback actuator positioner control system 205 to exert a very specific and precise level of force directly to lever arm horizontal component 215 of magnetic force feedback actuator positioner-controlled transducer lever arm 211 which, in turn, provides a constant pressure on transducer element support 213 of magnetic force feedback actuator positioner-controlled transducer lever arm 211 and transducer wheel 110 and adjust the applied force to changes in sheet of material surface/thickness, wheel eccentricities, and the introduction of a sheet of material almost instantaneously and without the recovery/bounce issues of prior at systems.

As noted above, in various embodiments, magnetic force feedback actuator positioner system 201 and magnetic force feedback actuator positioner 203 can be any of several magnetic force feedback actuator positioners and systems known in the art and that are commercially available from several manufactures. Consequently, the structure and operation of magnetic force feedback actuator positioner systems and magnetic force feedback actuator positioners is known. Therefore, a more detailed discussion of any specific magnetic force feedback actuator positioners and systems is omitted here to avoid detracting from the general description of the disclosed embodiments.

The disclosed use of magnetic force feedback actuator positioner system 201 and magnetic force feedback actuator positioner 203 provides not only for a method and system to maintain a precise and constant force between the surface of a sheet of material and a transducer element, but it also provide reaction times that can allow for adjustment to the introduction of a sheet of material into the position between transducer element and a lift element, and/or variations in the surface of a sheet of material, in nearly real time to all but eliminate the bounce/recovery oscillations associated with prior art ultrasonic density detection systems. Consequently, the disclosed embodiments can obtain precise density measurements of an entire sheet of material without loss of data and with unprecedented accuracy unobtainable using prior art ultrasonic density detection systems.

In addition, in one embodiment, magnetic force feedback actuator positioner system 201 and magnetic force feedback actuator positioner 203 can provide accurate displacement information for thickness measurement superior to prior art ultrasonic density detection systems by using current prior art transducer lever arm thickness/displacement sensors to detect the movement of prior art transducer lever arm vertical thickness measurement components.

In addition, in one embodiment, magnetic force feedback actuator positioner system 201 and magnetic force feedback actuator positioner 203 utilizes an integral displacement system to detect the presence of a sheet of material to trigger the transmitting transducer element to begin operation. This internal measurement ability of the magnetic force feedback actuator positioner can accurately and rapidly trigger pulse transmission as a result of displacement without using prior art switching mechanisms. Therefore, using the disclosed embodiments, the reliability and efficiency of operation is greatly increased compared to prior art ultrasonic density detection systems that can be falsely triggered by trash on the conveyor line.

As discussed in more detail below, the disclosed embodiments utilizing magnetic force feedback actuator positioner system 201 and magnetic force feedback actuator positioner 203 are able to provide the precise, consistent, and accurate density readings now needed/required in many industries. In addition, the disclosed embodiments utilizing magnetic force feedback actuator positioner system 201 and magnetic force feedback actuator positioner 203 have fewer parts and components than prior art ultrasonic density detection systems and are therefore less subject to failure, are lighter, and require less maintenance Consequently, the disclosed embodiments utilizing magnetic force feedback actuator positioner system 201 and magnetic force feedback actuator positioner 203 are more efficient and effective, than prior art ultrasonic density detection systems and are less expensive to operate.

Figure 4:
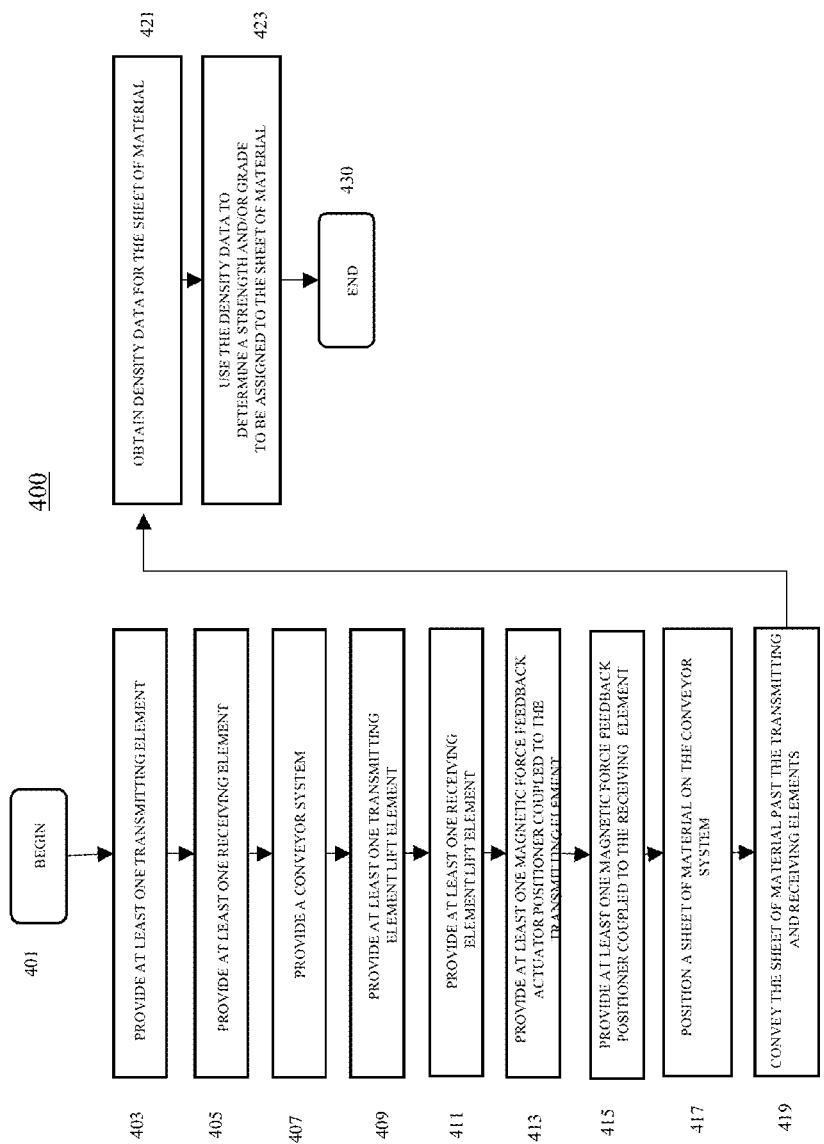
FIG. 4 is a simplified flow chart representing one embodiment of the disclosed method for determining the density of a sheet of material.

FIG. 4 is a simplified flow chart representing one embodiment of the disclosed method 400 for determining the density of a sheet of material.

As seen in FIG. 4, in one embodiment, the disclosed method 400 for determining the density of a sheet of material begins 401 and process flow proceeds to 403.

In one embodiment, at 403 at least one transmitting transducer element is provided. In one embodiment, the at least one transmitting transducer element is contained in a provided transmitting transducer element wheel.

In one embodiment, once at least one transmitting transducer element is provided at 403, process flow proceeds to 405. In one embodiment, at 405 at least one receiving transducer element is provided. In one embodiment, the at least one receiving transducer element is contained in a provided receiving transducer element wheel.

In one embodiment, the receiving transducer element is positioned a defined distance from the transmitting transducer element for receiving the ultrasonic signals from the transmitting transducer element.

In one embodiment, once at least one receiving transducer element is provided at 405, process flow proceeds to 407. In one embodiment, at 407 a conveyor system is provided to convey a sheet of material to the transmitting transducer element and the receiving transducer element.

In one embodiment, once a conveyor system is provided to convey a sheet of material to the transmitting transducer element and the receiving transducer element at 407, process flow proceeds to 409. In one embodiment, at 409 at least one transmitting transducer lift element is provided and positioned such that a sheet of material passes between the transmitting transducer element and the transmitting transducer lift element as the conveyor system conveys the sheet of material past the transmitting transducer element and the receiving transducer element. In one embodiment, the at least one transmitting transducer lift element is transmitting transducer lift wheel.

In one embodiment, once at least one transmitting transducer lift element is provided at 409, process flow proceeds to 411. In one embodiment, at 411 at least one receiving transducer lift element is provided and positioned such that a sheet of material passes between the receiving transducer element and the transmitting transducer lift element as the conveyor system conveys the sheet of material past the transmitting transducer element and the receiving transducer element.

In one embodiment, once at least one receiving transducer lift wheel is provided at 411, process flow proceeds to 413. In one embodiment, at 413 at least one magnetic force feedback actuator positioner is provided and operationally coupled to the transmitting transducer element to apply a selected constant force on the transmitting transducer element and maintain a constant pressure of the transmitting transducer element on the first portion of the surface of a sheet of material as the sheet of material is conveyed by the conveyor system past the transmitting transducer element and the receiving transducer element. In one embodiment, the at least one receiving transducer lift element is receiving transducer lift wheel.

In one embodiment, once at least one magnetic force feedback actuator positioner is provided and operationally coupled to the transmitting transducer element at 413, process flow proceeds to 415. In one embodiment, at 415 at least one magnetic force feedback actuator positioner is provided and operationally coupled to the receiving transducer element to apply a selected constant force on the receiving transducer element and maintain a constant pressure of the receiving transducer element on the second portion of the surface of a sheet of material as the sheet of material is conveyed by the conveyor system past the transmitting transducer wheel and the receiving transducer element.

Of note, in one embodiment, the at least one magnetic force feedback actuator positioner of 413 and the at least one magnetic force feedback actuator positioner of 413 can a single magnetic force feedback actuator positioner. In other embodiments, the at least one magnetic force feedback actuator positioner of 413 and the at least one magnetic force feedback actuator positioner of 413 can be separate magnetic force feedback actuator positioners. In some embodiments, the at least one magnetic force feedback actuator positioner of 413 and the at least one magnetic force feedback actuator positioner of 413 are controlled by separate control systems. In other embodiments, the at least one magnetic force feedback actuator positioner of 413 and the at least one magnetic force feedback actuator positioner of 413 are controlled in tandem by one or more control systems.

In one embodiment, once at least one magnetic force feedback actuator positioner is provided and operationally coupled to the receiving transducer element at 415 process flow proceeds to 417. In one embodiment, at 417 a sheet of material is positioned on the conveyor system of 407.

In one embodiment, the sheet of material is a sheet of wood product. In one embodiment, the sheet of material is a sheet of veneer.

In one embodiment, once the sheet of material is positioned on the conveyor system of at 417, process flow proceeds to 419. In one embodiment, at 419 the conveyor system conveys the sheet of material past the transmitting transducer element and the receiving transducer element. In one embodiment, as the conveyor system conveys the sheet of material past the transmitting transducer element and the receiving transducer element, a first portion of a surface of the sheet of material is positioned between the transmitting transducer element and the transmitting transducer lift element and, simultaneously, a second portion of a surface of the sheet of material is positioned between the receiving transducer element and receiving transducer lift element.

In one embodiment, as the conveyor system conveys the sheet of material past the transmitting transducer element and the receiving transducer element, the at least one magnetic force feedback actuator positioner coupled to the transmitting transducer element applies and maintains the selected constant force on the transmitting transducer element and maintains a constant pressure of the transmitting transducer element on the first portion of the surface of a sheet of material.

In addition, as the conveyor system conveys the sheet of material past the transmitting transducer element and the receiving transducer element, the at least one magnetic force feedback actuator positioner coupled to the receiving transducer element applies and maintains the selected constant force on the receiving transducer element and maintains a constant pressure of the receiving transducer element on the second portion of the surface of a sheet of material.

As noted above, in one embodiment, the at least one magnetic force feedback actuator positioner of 413 and the at least one magnetic force feedback actuator positioner of 413 can a single magnetic force feedback actuator positioner. In other embodiments, the at least one magnetic force feedback actuator positioner of 413 and the at least one magnetic force feedback actuator positioner of 413 can be separate magnetic force feedback actuator positioners. In some embodiments, the at least one magnetic force feedback actuator positioner of 413 and the at least one magnetic force feedback actuator positioner of 413 are controlled by separate control systems. In other embodiments, the at least one magnetic force feedback actuator positioner of 413 and the at least one magnetic force feedback actuator positioner of 413 are controlled in tandem by a common control system.

In one embodiment, once the conveyor system conveys the sheet of material past the transmitting transducer element and the receiving transducer element at 419, process flow proceeds to 421. In one embodiment, at 421 density data for the sheet of material is obtained.

In one embodiment, at 421, as the conveyor system conveys the sheet of material past the transmitting transducer element and the receiving transducer element, ultrasonic signals are generated and transmitted from the transmitting transducer element. The ultrasonic signals enter the sheet of material at the first portion of the surface of the sheet of material and passes through the sheet of material to be received by the receiving transducer element at the second portion of the surface of the sheet of material.

In one embodiment, based on a time the ultrasonic signals take to move from the transmitting transducer element at first portion of the surface of the sheet of material, pass through the sheet of material, and then be received by the receiving transducer element at the second portion of the surface of the sheet of material, density data for the sheet of material can be determined.

In one embodiment, once density data for the sheet of material is obtained at 421, process flow proceeds to 423. In one embodiment, at 423 the strength of the sheet of material is determined and/or a grade assigned to the sheet of material that is used to determine how the sheet of material can be used.

In one embodiment, at 423 the density data obtained using the disclosed method for determining the density of a sheet of material at 421 is used to determine the strength of the sheet of material. In one embodiment, density data obtained using the disclosed method for determining the density of a sheet of material is used, at least in part, to determine a grade assigned to the sheet of material. In one embodiment, the grade assigned to the sheet of material is used to determine how the sheet of material is used.

In one embodiment, once the strength of the sheet of material is determined and/or a grade assigned to the sheet of material that is used to determine how the sheet of material can be used at 423, process flow proceeds to 430. In one embodiment, at 430, method 400 is exited to await the introduction of the next sheet of material.

As discussed above, the disclosed embodiments utilize one or more magnetic force feedback actuator positioners to accurately maintain a constant selected pressure/force between transducer elements and the surface of a sheet of material as the sheet of material moves through the position between a transmitting transducer element and/or a receiver transducer element. Consequently, according to the disclosed embodiments, the antiquated mechanical/pneumatic springs/airbags of prior art ultrasonic density detection systems are replaced with a highly responsive magnetic force feedback actuator positioner.

The disclosed use of a magnetic force feedback actuator positioner provides not only for a method and system to maintain a precise and constant force between the surface of a sheet of material and a transducer element, but it also provides reaction times that can allow for adjustment to the introduction of a sheet of material into the position between transducer element and a lift element, and/or variations in the surface of a sheet of material, in nearly real time to all but eliminate the bounce/recovery oscillations associated with prior art ultrasonic density detection systems. Consequently, the disclosed embodiments can obtain precise density measurements of an entire sheet of material without loss of data and with unprecedented accuracy unobtainable using prior art ultrasonic density detection systems.

In addition, in one embodiment, the magnetic force feedback actuator positioner can provide accurate displacement information for thickness measurement superior to prior art ultrasonic density detection systems by using current prior art transducer lever arm thickness/displacement sensors to detect the movement of prior art transducer lever arm vertical thickness measurement components.

In addition, in one embodiment, the magnetic force feedback actuator positioner utilizes an internal displacement/photo switch to detect the presence of a sheet of material to trigger the transmitting transducer wheel to begin operation. This internal measurement ability of the magnetic force feedback actuator positioner can accurately and rapidly trigger pulse transmission as a result of displacement. Therefore, using the disclosed embodiments, the reliability and efficiency of operation is greatly increased compared to prior art ultrasonic density detection systems that can be falsely triggered by trash on the conveyor line.

By maintaining a precise constant pressure/force on transducer wheels, and therefore keeping the pressure/force of the transducer wheels on the surface of sheet of material constant, the disclosed use of magnetic force feedback actuator positioner provides an accuracy and reliability of density measurements unobtainable using prior art ultrasonic density detection systems. This is accomplished by eliminating the relatively antiquated mechanical/pneumatic prior art pneumatic position system air bag and spring systems. This, in turn eliminates the prior art PSI and gauge errors inherent in prior art ultrasonic density detection systems and the resulting significant variance in density readings from actual density from pulse to pulse in the same sheet of material.

In addition, the disclosed use of magnetic force feedback actuator positioner provides for simple and precise force/pressure adjustments for various types of material making up sheets of material. In addition, the disclosed use of magnetic force feedback actuator positioner provides for the precise adjustment of applied pressure/force to compensate for lift wheel eccentricity due to manufacturing imperfections and wear and tear resulting from the rebound force.

In addition, the disclosed use of magnetic force feedback actuator positioner eliminates the need for prior art transducer lever arm thickness/displacement sensors and prior art transducer lever arm vertical thickness measurement components. This results in a simpler, lighter, and less failure prone system that require less maintenance.

In addition, the disclosed use of magnetic force feedback actuator positioner eliminates the need for prior art sheet of material detector. This eliminates yet more components that need to be maintained, are subject to failure, and are subject to false indicators using prior art ultrasonic density detection systems.

Consequently, the disclosed embodiments utilizing a magnetic force feedback actuator positioner are able to provide the precise, consistent, and accurate density readings now needed/required in many industries. In addition, the disclosed embodiments utilizing a magnetic force feedback actuator positioner have fewer parts and components than prior art ultrasonic density detection systems and are therefore less subject to failure, are lighter, and require less maintenance Consequently, the disclosed embodiments utilizing a magnetic force feedback actuator positioner are more efficient and effective, than prior art ultrasonic density detection systems and are less expensive to operate.

In one embodiment, a system for determining the density of a sheet of material is disclosed that includes a density analysis station. In one embodiment, the density analysis station includes at least one transmitting transducer element for generating and transmitting ultrasonic signals.

In one embodiment, the density analysis station also includes at least one receiving transducer element positioned a defined/known distance from the transmitting transducer element for receiving the ultrasonic signals from the transmitting transducer element.

In one embodiment, a conveyor system is used to convey a sheet of material through the density analysis station. In one embodiment, as the conveyor system conveys the sheet of material through the density analysis station the transmitting transducer element is in contact with a first portion of a surface of the sheet of material and the receiving transducer element is in contact with a second portion of the surface of the sheet of material at the defined/known distance from the first portion of the surface of the sheet of material.

In one embodiment, ultrasonic signals are generated and transmitted from the transmitting transducer element into the sheet of material at the first portion of the surface of the sheet of material and pass through the sheet of material to be received by the receiving transducer element at the second portion of the surface of the sheet of material.

In one embodiment, at least one magnetic force feedback actuator positioner is operationally coupled to the transmitting transducer element. In one embodiment, the at least one magnetic force feedback actuator positioner is used to apply and maintain a selected constant force on the transmitting transducer element to maintain a constant pressure of transmitting transducer element on the first portion of the surface of the sheet of material as the sheet of material is conveyed by the conveyor system through the density analysis station.

In one embodiment, a transmitting transducer element lever arm is operationally coupled to the at least one magnetic force feedback actuator positioner. In one embodiment, the transmitting transducer element lever arm is also operationally coupled to the transmitting transducer element. In this way the at least one magnetic force feedback actuator positioner applies and maintains a selected force on the transmitting transducer element through the transmitting transducer element lever arm to keep a selected pressure between the transmitting transducer element and the first portion of the surface of the sheet of material.

In one embodiment, at least one magnetic force feedback actuator positioner is operationally coupled to the receiving transducer element to apply and maintain a selected constant force on the receiving transducer element. In this way a constant pressure of the receiving transducer element on the second portion of the surface of the sheet of material is maintained as the sheet of material is conveyed by the conveyor system through the density analysis station.

In one embodiment, the at least one magnetic force feedback actuator positioner operationally coupled to the transmitting transducer element and the at least one magnetic force feedback actuator positioner operationally coupled to the receiving transducer element are controlled to operate in tandem by a common magnetic force feedback actuator positioner control system.

In one embodiment, a receiving transducer element lever arm is operationally coupled to at least one magnetic force feedback actuator positioner and the receiving transducer element lever arm is also operationally coupled to the receiving transducer element. In this way the at least one magnetic force feedback actuator positioner applies and maintains a selected force on the receiving transducer element through the receiving transducer element lever arm to keep a selected pressure between the receiving transducer element and the second portion of the surface of the sheet of material.

In one embodiment, the transmitting transducer element for generating and transmitting ultrasonic signals is contained in a transmitting transducer wheel and as the conveyor system conveys the sheet of material through the density analysis station the transmitting transducer wheel is in contact with a first portion of a surface of the sheet of material and the receiving transducer element is in contact with a second portion of the surface of the sheet of material at the defined/known distance from the first portion of the surface of the sheet of material. In one embodiment, ultrasonic signals generated and transmitted from the transmitting transducer element in the transmitting transducer wheel enter the sheet of material at the first portion of the surface of the sheet of material and pass through the sheet of material to be received by the receiving transducer element at the second portion of the surface of the sheet of material.

In one embodiment, the sheet of material is a sheet of wood product. In one embodiment, the sheet of material is a sheet of veneer.

In one embodiment, density data obtained using the disclosed system for determining the density of a sheet of material is used to determine the strength of the sheet of material. In one embodiment, density data obtained using the disclosed system for determining the density of a sheet of material is used, at least in part, to determine a grade assigned to the sheet of material. In one embodiment, the grade assigned to the sheet of material is used to determine how the sheet of material is used.

In one embodiment, a system for determining the density of a sheet of material is disclosed that includes at least one transmitting transducer wheel. In one embodiment, the transmitting transducer wheel includes a transmitting transducer element for generating and transmitting ultrasonic signals.

In one embodiment, the disclosed system for determining the density of a sheet of material includes at least one receiving transducer element. In one embodiment, the receiving transducer element is positioned a defined/known distance from the transmitting transducer wheel for receiving the ultrasonic signals from the transmitting transducer element in the transmitting transducer wheel.

In one embodiment, a conveyor system is used to convey a sheet of material to the transmitting transducer wheel and the receiving transducer element. In one embodiment, as the conveyor system conveys the sheet of material to the transmitting transducer wheel and the receiving transducer element, the transmitting transducer wheel is in contact with a first portion of a surface of the sheet of material and the receiving transducer element is in contact with a second portion of the surface of the sheet of material at the same time at the defined/known distance from the first portion of the surface of the sheet of material.

In one embodiment, the ultrasonic signals generated and transmitted from the transmitting transducer element of the transmitting transducer wheel enter the sheet of material at the first portion of the surface of the sheet of material and pass through the sheet of material to be received by the receiving transducer element at the second portion of the surface of the sheet of material.

In one embodiment, at least one magnetic force feedback actuator positioner is operationally coupled to the transmitting transducer wheel to apply a selected constant force on the transmitting transducer wheel and maintain a constant pressure of the transmitting transducer wheel on the first portion of the surface of the sheet of material as the sheet of material is conveyed by the conveyor system through the density analysis station.

In one embodiment, at least one magnetic force feedback actuator positioner is operationally coupled to the receiving transducer element to apply a selected constant force on the receiving transducer element and maintain a constant pressure of the receiving transducer element on the second portion of the surface of the sheet of material as the sheet of material is conveyed by the conveyor system through the density analysis station.

In one embodiment, a transmitting transducer element lever arm is operationally coupled to the at least one magnetic force feedback actuator positioner and the transmitting transducer wheel. In this way the at least one magnetic force feedback actuator positioner is used to apply a selected force on the transmitting transducer wheel through the transmitting transducer element lever arm to keep a selected pressure between the transmitting transducer wheel and the first portion of the surface of the sheet of material.

In one embodiment, a receiving transducer element lever arm is operationally coupled to the at least one magnetic force feedback actuator positioner and the receiving transducer element. In this way, the at least one magnetic force feedback actuator positioner is used to apply a selected force on the receiving transducer element through the receiving transducer element lever arm to keep a selected pressure between the receiving transducer element and the second portion of the surface of the sheet of material.

In one embodiment, the sheet of material is a sheet of wood product. In one embodiment, the sheet of material is a sheet of veneer.

In one embodiment, density data obtained using the disclosed system for determining the density of a sheet of material is used to determine the strength of the sheet of material. In one embodiment, density data obtained using the disclosed system for determining the density of a sheet of material is used, at least in part, to determine a grade assigned to the sheet of material. In one embodiment, the grade assigned to the sheet of material is used to determine how the sheet of material is used.

In one embodiment, a system for determining the density of a sheet of material is disclosed that includes at least one transmitting transducer wheel. In one embodiment, the transmitting transducer wheel includes a transmitting transducer element for generating and transmitting ultrasonic signals.

In one embodiment, the disclosed system for determining the density of a sheet of material includes at least one receiving transducer element, the receiving transducer element is positioned a defined/known distance from the transmitting transducer wheel for receiving the ultrasonic signals from the transmitting transducer element in the transmitting transducer wheel.

In one embodiment, a conveyor system is used to convey a sheet of material to the transmitting transducer wheel and the receiving transducer element. In one embodiment, as the conveyor system conveys the sheet of material to the transmitting transducer wheel and the receiving transducer element, the transmitting transducer wheel is in contact with a first portion of a surface of the sheet of material and the receiving transducer element is in contact with a second portion of the surface of the sheet of material at the same time at the defined/known distance from the first portion of the surface of the sheet of material.

In one embodiment, the ultrasonic signals generated and transmitted from the transmitting transducer element of the transmitting transducer wheel enter the sheet of material at the first portion of the surface of the sheet of material and pass through the sheet of material to be received by the receiving transducer element at the second portion of the surface of the sheet of material.

In one embodiment, at least one transmitting transducer lift wheel is positioned such that the sheet of material passes between the transmitting transducer wheel and the transmitting transducer lift wheel as the conveyor system conveys the sheet of material past the transmitting transducer wheel and the receiving transducer element.

In one embodiment, at least one magnetic force feedback actuator positioner is operationally coupled to the transmitting transducer wheel to apply a selected constant force on the transmitting transducer wheel and maintain a constant pressure of the transmitting transducer wheel on the first portion of the surface of the sheet of material as the sheet of material is conveyed by the conveyor system past the transmitting transducer wheel and the receiving transducer element.

In one embodiment, at least one magnetic force feedback actuator positioner is operationally coupled to the receiving transducer element to apply a selected constant force on the receiving transducer element to maintain a constant pressure of the receiving transducer element on the second portion of the surface of the sheet of material as the sheet of material is conveyed by the conveyor system through the past the transmitting transducer wheel and the receiving transducer element.

In one embodiment, the receiving transducer element for receiving the ultrasonic signals is contained in a receiving transducer wheel.

In one embodiment, at least one receiving transducer lift wheel is positioned such that the sheet of material passes between the receiving transducer wheel and the receiving transducer lift wheel as the conveyor system conveys the sheet of material to the transmitting transducer wheel and the receiving transducer wheel.

In one embodiment, a transmitting transducer element lever arm is operationally coupled to the at least one magnetic force feedback actuator positioner and the transmitting transducer wheel. In this way the at least one magnetic force feedback actuator positioner is used to apply a selected force on the transmitting transducer wheel through the transmitting transducer element lever arm to keep a selected pressure between the transmitting transducer wheel and the first portion of the surface of the sheet of material.

In one embodiment, a receiving transducer element lever arm is operationally coupled to the at least one magnetic force feedback actuator positioner and the receiving transducer wheel. In this way, the at least one magnetic force feedback actuator positioner is used to apply a selected force on the receiving transducer wheel through the receiving transducer element lever arm to keep a selected pressure between the receiving transducer wheel and the second portion of the surface of the sheet of material.

In one embodiment, the sheet of material is a sheet of wood product. In one embodiment, the sheet of material is a sheet of veneer.

In one embodiment, density data obtained using the disclosed system for determining the density of a sheet of material is used to determine the strength of the sheet of material. In one embodiment, density data obtained using the disclosed system for determining the density of a sheet of material is used, at least in part, to determine a grade assigned to the sheet of material. In one embodiment, the grade assigned to the sheet of material is used to determine how the sheet of material is used.

In one embodiment, a method for determining the density of a sheet of material is disclosed that includes providing a density analysis station. In one embodiment, the density analysis station includes at least one transmitting transducer element for generating and transmitting ultrasonic signals.

In one embodiment, the density analysis station also includes at least one receiving transducer element positioned a defined/known distance from the transmitting transducer element for receiving the ultrasonic signals from the transmitting transducer element.

In one embodiment, a conveyor system is provided to convey a sheet of material through the density analysis station. In one embodiment, as the conveyor system conveys the sheet of material through the density analysis station the transmitting transducer element is in contact with a first portion of a surface of the sheet of material and the receiving transducer element is in contact with a second portion of the surface of the sheet of material at the defined/known distance from the first portion of the surface of the sheet of material.

In one embodiment, ultrasonic signals are generated and transmitted from the transmitting transducer element into the sheet of material at the first portion of the surface of the sheet of material and pass through the sheet of material to be received by the receiving transducer element at the second portion of the surface of the sheet of material.

In one embodiment, the method for determining the density of a sheet of material includes providing at least one magnetic force feedback actuator positioner.

In one embodiment, the method for determining the density of a sheet of material includes operationally coupling the at least one magnetic force feedback actuator positioner to the transmitting transducer element. In one embodiment, the at least one magnetic force feedback actuator positioner is used to apply and maintain a selected constant force on the transmitting transducer element to maintain a constant pressure of transmitting transducer element on the first portion of the surface of the sheet of material as the sheet of material is conveyed by the conveyor system through the density analysis station.

In one embodiment, a transmitting transducer element lever arm is provided and operationally coupled to the at least one magnetic force feedback actuator positioner. In one embodiment, the transmitting transducer element lever arm is also operationally coupled to the transmitting transducer element. In this way the at least one magnetic force feedback actuator positioner applies and maintains a selected force on the transmitting transducer element through the transmitting transducer element lever arm to keep a selected pressure between the transmitting transducer element and the first portion of the surface of the sheet of material.

In one embodiment, at least one magnetic force feedback actuator positioner is provided and operationally coupled to the receiving transducer element to apply and maintain a selected constant force on the receiving transducer element. In this way a constant pressure of the receiving transducer element on the second portion of the surface of the sheet of material is maintained as the sheet of material is conveyed by the conveyor system through the density analysis station.

In one embodiment, a magnetic force feedback actuator positioner control system is provided. In one embodiment, the at least one magnetic force feedback actuator positioner operationally coupled to the transmitting transducer element and the at least one magnetic force feedback actuator positioner operationally coupled to the receiving transducer element are controlled to operate in tandem by a single magnetic force feedback actuator positioner control system.

In one embodiment, a receiving transducer element lever arm is provided and operationally coupled to at least one magnetic force feedback actuator positioner and the receiving transducer element lever arm is also operationally coupled to the receiving transducer element. In this way the at least one magnetic force feedback actuator positioner applies and maintains a selected force on the receiving transducer element through the receiving transducer element lever arm to keep a selected pressure between the receiving transducer element and the second portion of the surface of the sheet of material.

In one embodiment, the transmitting transducer element for generating and transmitting ultrasonic signals is contained in a transmitting transducer wheel and as the conveyor system conveys the sheet of material through the density analysis station the transmitting transducer wheel is in contact with a first portion of a surface of the sheet of material and the receiving transducer element is in contact with a second portion of the surface of the sheet of material at the defined/known distance from the first portion of the surface of the sheet of material. In one embodiment, ultrasonic signals generated and transmitted from the transmitting transducer element in the transmitting transducer wheel enter the sheet of material at the first portion of the surface of the sheet of material and pass through the sheet of material to be received by the receiving transducer element at the second portion of the surface of the sheet of material.

In one embodiment, the sheet of material is a sheet of wood product. In one embodiment, the sheet of material is a sheet of veneer.

In one embodiment, density data obtained using the disclosed method for determining the density of a sheet of material is used to determine the strength of the sheet of material. In one embodiment, density data obtained using the disclosed method for determining the density of a sheet of material is used, at least in part, to determine a grade assigned to the sheet of material. In one embodiment, the grade assigned to the sheet of material is used to determine how the sheet of material is used.

In one embodiment, a method for determining the density of a sheet of material is disclosed that includes providing at least one transmitting transducer wheel. In one embodiment, the transmitting transducer wheel includes a transmitting transducer element for generating and transmitting ultrasonic signals.

In one embodiment, the disclosed method for determining the density of a sheet of material includes at least one receiving transducer element. In one embodiment, the disclosed method for determining the density of a sheet of material includes positioning the receiving transducer element a defined/known distance from the transmitting transducer wheel for receiving the ultrasonic signals from the transmitting transducer element in the transmitting transducer wheel.

In one embodiment, a conveyor system is provided. In one embodiment, the conveyor system is used to convey a sheet of material to the transmitting transducer wheel and the receiving transducer element.

In one embodiment, as the conveyor system conveys the sheet of material to the transmitting transducer wheel and the receiving transducer element, the transmitting transducer wheel is in contact with a first portion of a surface of the sheet of material and the receiving transducer element is in contact with a second portion of the surface of the sheet of material at the same time and at the defined/known distance from the first portion of the surface of the sheet of material.

In one embodiment, the ultrasonic signals generated and transmitted from the transmitting transducer element of the transmitting transducer wheel enter the sheet of material at the first portion of the surface of the sheet of material and pass through the sheet of material to be received by the receiving transducer element at the second portion of the surface of the sheet of material.

In one embodiment, at least one magnetic force feedback actuator positioner is provided and operationally coupled to the transmitting transducer wheel to apply a selected constant force on the transmitting transducer wheel and maintain a constant pressure of the transmitting transducer wheel on the first portion of the surface of the sheet of material as the sheet of material is conveyed by the conveyor system through the density analysis station.

In one embodiment, at least one magnetic force feedback actuator positioner is provided and operationally coupled to the receiving transducer element to apply a selected constant force on the receiving transducer element and maintain a constant pressure of the receiving transducer element on the second portion of the surface of the sheet of material as the sheet of material is conveyed by the conveyor system through the density analysis station.

In one embodiment, a transmitting transducer element lever arm is provided and operationally coupled to the at least one magnetic force feedback actuator positioner and the transmitting transducer wheel. In this way the at least one magnetic force feedback actuator positioner is used to apply a selected force on the transmitting transducer wheel through the transmitting transducer element lever arm to keep a selected pressure between the transmitting transducer wheel and the first portion of the surface of the sheet of material.

In one embodiment, a receiving transducer element lever arm is provided and operationally coupled to the at least one magnetic force feedback actuator positioner and the receiving transducer element. In this way, the at least one magnetic force feedback actuator positioner is used to apply a selected force on the receiving transducer element through the receiving transducer element lever arm to keep a selected pressure between the receiving transducer element and the second portion of the surface of the sheet of material.

In one embodiment, the sheet of material is a sheet of wood product. In one embodiment, the sheet of material is a sheet of veneer.

In one embodiment, density data obtained using the disclosed method for determining the density of a sheet of material is used to determine the strength of the sheet of material. In one embodiment, density data obtained using the disclosed method for determining the density of a sheet of material is used, at least in part, to determine a grade assigned to the sheet of material. In one embodiment, the grade assigned to the sheet of material is used to determine how the sheet of material is used.

In one embodiment, a method for determining the density of a sheet of material is disclosed that includes providing at least one transmitting transducer wheel. In one embodiment, the transmitting transducer wheel includes a transmitting transducer element for generating and transmitting ultrasonic signals.

In one embodiment, the disclosed method for determining the density of a sheet of material includes providing at least one receiving transducer element. In one embodiment, the receiving transducer element is positioned a defined/known distance from the transmitting transducer wheel for receiving the ultrasonic signals from the transmitting transducer element in the transmitting transducer wheel.

In one embodiment, a conveyor system is provided and used to convey a sheet of material to the transmitting transducer wheel and the receiving transducer element. In one embodiment, as the conveyor system conveys the sheet of material to the transmitting transducer wheel and the receiving transducer element, the transmitting transducer wheel is in contact with a first portion of a surface of the sheet of material and the receiving transducer element is in contact with a second portion of the surface of the sheet of material at the same time and at the defined/known distance from the first portion of the surface of the sheet of material.

In one embodiment, the ultrasonic signals generated and transmitted from the transmitting transducer element of the transmitting transducer wheel enter the sheet of material at the first portion of the surface of the sheet of material and pass through the sheet of material to be received by the receiving transducer element at the second portion of the surface of the sheet of material.

In one embodiment, at least one transmitting transducer lift wheel is provided and positioned such that the sheet of material passes between the transmitting transducer wheel and the transmitting transducer lift wheel as the conveyor system conveys the sheet of material past the transmitting transducer wheel and the receiving transducer element.

In one embodiment, at least one magnetic force feedback actuator positioner is provided and operationally coupled to the transmitting transducer wheel to apply a selected constant force on the transmitting transducer wheel and maintain a constant pressure of the transmitting transducer wheel on the first portion of the surface of the sheet of material as the sheet of material is conveyed by the conveyor system past the transmitting transducer wheel and the receiving transducer element.

In one embodiment, at least one magnetic force feedback actuator positioner is provided and operationally coupled to the receiving transducer element to apply a selected constant force on the receiving transducer element to maintain a constant pressure of the receiving transducer element on the second portion of the surface of the sheet of material as the sheet of material is conveyed by the conveyor system through the past the transmitting transducer wheel and the receiving transducer element.

In one embodiment, a receiving transducer wheel is provided. In one embodiment, the receiving transducer element for receiving the ultrasonic signals is contained in a receiving transducer wheel.

In one embodiment, at least one receiving transducer lift wheel is provided and positioned such that the sheet of material passes between the receiving transducer wheel and the receiving transducer lift wheel as the conveyor system conveys the sheet of material to the transmitting transducer wheel and the receiving transducer wheel.

In one embodiment, a transmitting transducer element lever arm is provided and operationally coupled to the at least one magnetic force feedback actuator positioner and the transmitting transducer wheel. In this way the at least one magnetic force feedback actuator positioner is used to apply a selected force on the transmitting transducer wheel through the transmitting transducer element lever arm to keep a selected pressure between the transmitting transducer wheel and the first portion of the surface of the sheet of material.

In one embodiment, a receiving transducer element lever arm is provided and operationally coupled to the at least one magnetic force feedback actuator positioner and the receiving transducer wheel. In this way, the at least one magnetic force feedback actuator positioner is used to apply a selected force on the receiving transducer wheel through the receiving transducer element lever arm to keep a selected pressure between the receiving transducer wheel and the second portion of the surface of the sheet of material.

In one embodiment, the sheet of material is a sheet of wood product. In one embodiment, the sheet of material is a sheet of veneer.

In one embodiment, density data obtained using the disclosed method for determining the density of a sheet of material is used to determine the strength of the sheet of material. In one embodiment, density data obtained using the disclosed method for determining the density of a sheet of material is used, at least in part, to determine a grade assigned to the sheet of material. In one embodiment, the grade assigned to the sheet of material is used to determine how the sheet of material is used.

Consequently, using the disclosed embodiments, many of the shortcomings of prior art are minimized or by-passed/resolved.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

In addition, the operations shown in the figures, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A system comprising:

a density analysis station, the density analysis station including at least one transmitting transducer element, the transmitting transducer element generating and transmitting ultrasonic signals, the density analysis station including at least one receiving transducer element, the receiving transducer element being positioned a defined distance from the transmitting transducer element for receiving the ultrasonic signals from the transmitting transducer element;

a conveyor system for conveying a sheet of material through the density analysis station such that as the conveyor system conveys the sheet of material through the density analysis station the transmitting transducer element is in contact with a first portion of a surface of the sheet of material and the receiving transducer element is in contact with a second portion of the surface of the sheet of material at the defined distance from the first portion of the surface of the sheet of material such that ultrasonic signals generated and transmitted from the transmitting transducer element enter the sheet of material at the first portion of the surface of the sheet of material and pass through the sheet of material to be received by the receiving transducer element at the second portion of the surface of the sheet of material wherein a time interval between when the ultrasonic signals generated and transmitted from the transmitting transducer element enter the sheet of material at the first portion of the surface of the sheet of material and when the ultrasonic signals are received by the receiving transducer element at the second portion of the surface of the sheet of material is recorded and used to calculate the density of the sheet of material; and at least one magnetic force feedback actuator positioner operationally coupled to the transmitting transducer element to apply a selected force on the transmitting transducer element to maintain a selected pressure of transmitting transducer element on the first portion of the surface of the sheet of material as the sheet of material is conveyed by the conveyor system through the density analysis station.

2. The system of claim 1 further comprising:
a transmitting transducer element lever arm, the at least one magnetic force feedback actuator positioner operationally coupled to the transmitting transducer element lever arm and the transmitting transducer element lever arm operationally coupled to the transmitting transducer element to apply a selected force on the transmitting transducer element to keep a selected pressure between the transmitting transducer element and the first portion of the surface of the sheet of material.

3. The system of claim 1 further comprising:
the at least one magnetic force feedback actuator positioner operationally coupled to the receiving transducer element to apply a selected force on the receiving transducer element to maintain a selected pressure of the receiving transducer element on the second portion of the surface of the sheet of material as the sheet of material is conveyed by the conveyor system through the density analysis station.

4. The system of claim 3 wherein the at least one magnetic force feedback actuator positioner operationally coupled to the transmitting transducer element and the at least one magnetic force feedback actuator positioner operationally coupled to the receiving transducer element are controlled to operate in tandem by a magnetic force feedback actuator positioner control system.

5. The system of claim 1 further comprising:
a receiving transducer element lever arm, the at least one magnetic force feedback actuator positioner operationally coupled to the receiving transducer element lever arm and the receiving transducer element lever arm operationally coupled to the receiving transducer element to apply a selected force on the receiving transducer element to keep a selected pressure between the receiving transducer element and the second portion of the surface of the sheet of material.

6. The system of claim 1 wherein,
the transmitting transducer element for generating and transmitting ultrasonic signals is contained in a transmitting transducer wheel,
further wherein, as the conveyor system conveys the sheet of material through the density analysis station the transmitting transducer wheel is in contact with a first portion of a surface of the sheet of material and the receiving transducer element is in contact with a second portion of the surface of the sheet of material at the defined distance from the first portion of the surface of the sheet of material such that ultrasonic signals generated and transmitted from the transmitting transducer element in the transmitting transducer wheel enter the sheet of material at the first portion of the surface of the sheet of material and pass through the sheet of material to be received by the receiving transducer element at the second portion of the surface of the sheet of material.

7. The system of claim 1 wherein the sheet of material is a sheet of wood product.

8. The system of claim 1 wherein the sheet of material is a sheet of veneer.

9. A system for determining the density of a sheet of material comprising:
at least one transmitting transducer wheel, the transmitting transducer wheel including a transmitting transducer element, the transmitting transducer element generating and transmitting ultrasonic signals;
at least one receiving transducer element, the receiving transducer element being positioned a defined distance from the transmitting transducer wheel and receiving the ultrasonic signals from the transmitting transducer element in the transmitting transducer wheel;
a conveyor system for conveying a sheet of material to the transmitting transducer wheel and the receiving transducer element such that as the conveyor system conveys the sheet of material to the transmitting transducer wheel and the receiving transducer element, the transmitting transducer wheel is in contact with a first portion of a surface of the sheet of material and the receiving transducer element is in contact with a second portion of the surface of the sheet of material at the same time at the defined distance from the first portion of the surface of the sheet of material such that ultrasonic signals generated and transmitted from the transmitting transducer element of the transmitting transducer wheel enter the sheet of material at the first portion of the surface of the sheet of material and pass through the sheet of material to be received by the receiving transducer element at the second portion of the surface of the sheet of material wherein a time interval between when the ultrasonic signals generated and transmitted from the transmitting transducer element of the transmitting transducer wheel enter the sheet of material at the first portion of the surface of the sheet of material and when the ultrasonic signals are received by the receiving transducer element at the second portion of the surface of the sheet of material is recorded and used to calculate the density of the sheet of material;
at least one magnetic force feedback actuator positioner operationally coupled to the transmitting transducer wheel to apply a selected force on the transmitting transducer wheel to maintain a selected pressure of the transmitting transducer wheel on the first portion of the surface of the sheet of material as the sheet of material is conveyed by the conveyor system through the density analysis station; and
at least one magnetic force feedback actuator positioner operationally coupled to the receiving transducer element to apply a selected force on the receiving transducer element to maintain a selected pressure of the receiving transducer element on the second portion of the surface of the sheet of material as the sheet of material is conveyed by the conveyor system through the density analysis station.

10. The system of claim 9 further comprising:
a transmitting transducer element lever arm, the at least one magnetic force feedback actuator positioner operationally coupled to the transmitting transducer element lever arm and the transmitting transducer element lever arm operationally coupled to the transmitting transducer wheel to apply a selected force on the transmitting transducer wheel to keep a selected pressure between the transmitting transducer wheel and the first portion of the surface of the sheet of material.

11. The system of claim 9 further comprising:
a receiving transducer element lever arm, the at least one magnetic force feedback actuator positioner operationally coupled to the receiving transducer element lever arm and the receiving transducer element lever arm operationally coupled to the receiving transducer element to apply a selected force on the receiving transducer element to keep a selected pressure between the receiving transducer element and the second portion of the surface of the sheet of material.

12. The system of claim 9 wherein the sheet of material is a sheet of wood product.

13. The system of claim 9 wherein the sheet of material is a sheet of veneer.

14. A system for determining the density of a sheet of material comprising:
- at least one transmitting transducer wheel, the transmitting transducer wheel including a transmitting transducer element, the transmitting transducer element generating and transmitting ultrasonic signals;
- at least one receiving transducer element, the at least one receiving transducer element being positioned a defined distance from the transmitting transducer wheel for receiving the ultrasonic signals from the transmitting transducer element in the transmitting transducer wheel;
- a conveyor system for conveying a sheet of material to the transmitting transducer wheel and the receiving transducer element such that as the conveyor system conveys the sheet of material to the transmitting transducer wheel and the receiving transducer element the transmitting transducer wheel is in contact with a first portion of a surface of the sheet of material and the receiving transducer element is in contact with a second portion of the surface of the sheet of material at the same time at the defined distance from the first portion of the surface of the sheet of material such that ultrasonic signals generated and transmitted from the transmitting transducer element of the transmitting transducer wheel enter the sheet of material at the first portion of the surface of the sheet of material and pass through the sheet of material to be received by the receiving transducer element at the second portion of the surface of the sheet of material wherein a time interval between when the ultrasonic signals generated and transmitted from the transmitting transducer element of the transmitting transducer wheel enter the sheet of material at the first portion of the surface of the sheet of material and when the ultrasonic signals are received by the receiving transducer element at the second portion of the surface of the sheet of material is recorded and used to calculate the density of the sheet of material;
- at least one transmitting transducer lift wheel, the at least one transmitting transducer lift wheel positioned such that the sheet of material passes between the transmitting transducer wheel and the transmitting transducer lift wheel as the conveyor system conveys the sheet of material past the transmitting transducer wheel and the receiving transducer element;
- at least one magnetic force feedback actuator positioner operationally coupled to the transmitting transducer wheel to apply a selected force on the transmitting transducer wheel to maintain a selected pressure of transmitting transducer wheel on the first portion of the surface of the sheet of material as the sheet of material is conveyed by the conveyor system through the density analysis station; and
- at least one magnetic force feedback actuator positioner operationally coupled to the receiving transducer element to apply a selected force on the receiving transducer element to maintain a selected pressure of the receiving transducer element on the second portion of the surface of the sheet of material as the sheet of material is conveyed by the conveyor system past the transmitting transducer wheel and the receiving transducer element.

15. The system of claim 14 wherein the receiving transducer element for receiving the ultrasonic signals is contained in a receiving transducer wheel.

16. The system of claim 15 further comprising:
- at least one receiving transducer lift wheel, the at least one receiving transducer lift wheel positioned such that the sheet of material passes between the receiving transducer wheel and the receiving transducer lift wheel as the conveyor system conveys the sheet of material to the transmitting transducer wheel and the receiving transducer wheel.

17. The system of claim 14 further comprising:
- a transmitting transducer element lever arm, the at least one magnetic force feedback actuator positioner operationally coupled to the transmitting transducer element lever arm and the transmitting transducer element lever arm operationally coupled to the transmitting transducer wheel to apply a selected force on the transmitting transducer wheel to keep a selected pressure between the transmitting transducer wheel and the first portion of the surface of the sheet of material.

18. The system of claim 16 further comprising:
- a receiving transducer element lever arm, the at least one magnetic force feedback actuator positioner operationally coupled to the receiving transducer element lever arm and the receiving transducer element lever arm operationally coupled to the receiving transducer wheel to apply a selected force on the receiving transducer wheel to keep a selected pressure between the receiving transducer wheel and the second portion of the surface of the sheet of material.

19. The system of claim 14 wherein the sheet of material is a sheet of wood product.

20. The system of claim 14 wherein the sheet of material is a sheet of veneer.

* * * * *